(12) United States Patent
Guevremont et al.

(10) Patent No.: US 7,005,633 B2
(45) Date of Patent: Feb. 28, 2006

(54) METHOD AND APPARATUS FOR DESOLVATING IONS FOR INTRODUCTION INTO A FAIMS ANALYZER REGION

(75) Inventors: Roger Guevremont, Ottawa (CA); Randy Purves, Orleans (CA); David Barnett, Orleans (CA)

(73) Assignee: Ionalytics Corporation, Ottawa (CA)

( * ) Notice: Subject to any disclaimer, the term of this patent is extended or adjusted under 35 U.S.C. 154(b) by 1 day.

(21) Appl. No.: 10/503,659

(22) PCT Filed: Feb. 7, 2003

(86) PCT No.: PCT/CA03/00173

§ 371 (c)(1),
(2), (4) Date: Aug. 6, 2004

(87) PCT Pub. No.: WO03/067625

PCT Pub. Date: Aug. 14, 2003

(65) Prior Publication Data

US 2005/0178962 A1   Aug. 18, 2005

Related U.S. Application Data

(60) Provisional application No. 60/354,711, filed on Feb. 8, 2002.

(51) Int. Cl.
*H01J 49/40* (2006.01)
(52) U.S. Cl. .................................................. 250/287
(58) Field of Classification Search .................... None
See application file for complete search history.

(56) References Cited

U.S. PATENT DOCUMENTS 5,420,424 A   5/1995   Carnahan et al.

(Continued)

FOREIGN PATENT DOCUMENTS

WO   WO 00/63949   10/2000

(Continued)

OTHER PUBLICATIONS

Buryakov et al., "A New Method of Separation of Multi-Atomic Ions by Mobility at Atmospheric Pressure using a High-Frequency Amplitude-Asymmetric Strong Electric Field", Int. J. Mass Spectrom. Ion Processes, No. 128, pp. 143-148, (1993), Elsevier Science Publishers B.V.

(Continued)

*Primary Examiner*—Jack I. Berman
(74) *Attorney, Agent, or Firm*—Freedman & Associates

(57) ABSTRACT

Disclosed are an apparatus and a method for separating ions produced at an electrospray ionization source, based upon the high field mobility properties of the ions. An apparatus according to the instant invention includes a high field asymmetric waveform ion mobility spectrometer (FAIMS) having an analyzer region defined by a space between an inner electrode (32) and an outer electrode (34). In particular, the outer electrode includes an ion inlet (38) for introducing ions into a first portion of analyzer region and an ion outlet (56) for extracting ions from a second portion of the analyzer region. The FAIMS is characterized in that a gas-directing conduit (48) is provided through at least a portion of the inner electrode. In particular, the gas-directing conduit includes an opening at a first end thereof for supporting fluid communication between the gas-directing conduit and the first portion of the analyzer region. The gas-directing conduit is adapted at a second end thereof opposite the first end for supporting fluid communication between a gas source and the gas-directing conduit. The opening is orientated relative to the ion inlet such that gas provided through the gas-directing conduit flows partially outwardly from the analyzer region through the ion inlet, so as to desolvate the ions produced at an ionization source (42, 45) as they are introduced into the analyzer region.

46 Claims, 14 Drawing Sheets

U.S. PATENT DOCUMENTS

| | | |
|---|---|---|
| 5,723,861 A | 3/1998 | Carnahan et al. |
| 5,736,739 A | 4/1998 | Uber et al. |
| 6,495,823 B1 | 12/2002 | Miller et al. |
| 6,504,149 B1 | 1/2003 | Guevremont et al. |
| 6,512,224 B1 | 1/2003 | Miller et al. |
| 6,621,077 B1 | 9/2003 | Guevremont et al. |
| 6,690,004 B1 | 2/2004 | Miller et al. |
| 6,753,522 B1 | 6/2004 | Guevremont et al. |
| 2003/0038235 A1 * | 2/2003 | Guevremont et al. ....... 250/287 |
| 2003/0089847 A1 | 5/2003 | Guevremont et al. |
| 2003/0132380 A1 | 7/2003 | Miller et al. |
| 2003/0150985 A1 | 8/2003 | Guevremont et al. |
| 2003/0213899 A9 | 11/2003 | Guevremont |

FOREIGN PATENT DOCUMENTS

| | | | |
|---|---|---|---|
| WO | WO 01 69216 A | * | 9/2001 |
| WO | WO 01 69217 A | * | 9/2001 |
| WO | WO 01 69221 A | * | 9/2001 |
| WO | WO 03/067236 A2 | | 8/2003 |
| WO | WO 2004/030129 A2 | | 4/2004 |

OTHER PUBLICATIONS

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper #96-009, pp. 87-95, (1996), Framingham, MA, USA.

Purves et al., "Mass Spectrometric Characterization of a High-Field Asymmetric Waveform Ion Mobility Spectrometer", Review of Scientific Instruments, vol.69, No. 12, pp. 4094-4105, (Dec. 1998), American Institute of Physics.

Henderson et al., "ESI/Ion Trap/Ion Mobility/Time-of-Flight Mass Spectrometry for Rapid and Sensitive Analysis of Biomolecular Mixtures", Anal. Chem. 1999, vol. 71, No. 2, pp. 291-301, (Jan. 15, 1999), American Chemical Society.

Guevremont et al., "Atomspheric Pressure Ion Focusing in a High-Field Asymmetric Waveform Ion Mobility Spectrometer", Review of Scientific Instruments, vol. 70, No. 2, pp. 1370-1\383, (Feb. 1999), American Institute of Physics.

* cited by examiner

METHOD AND APPARATUS FOR DESOLVATING IONS FOR INTRODUCTION INTO A FAIMS ANALYZER REGION

This application claims the benefit of U.S. Provisional Application No. 60/354,711, filed Feb. 8, 2002.

FIELD OF THE INVENTION

The instant invention relates generally to high field asymmetric waveform ion mobility spectrometry (FAIMS), more particularly the instant invention relates to a FAIMS electrode assembly for supporting desolvation of electrosprayed ions absent a separate desolvation chamber.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in a FAIMS analyzer region on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected do voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position along the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

U.S. Pat. No. 5,420,424, issued to Carnahan and Tarassov on May 30, 1995, teaches a FAIMS device having cylindrical electrode geometry and electrometric ion detection, the contents of which are incorporated herein by reference. The FAIMS analyzer region is defined by an annular space between inner and outer cylindrical electrodes. In use, ions that are to be separated are entrained into a flow of a carrier gas and are carried into the analyzer region via an ion inlet orifice. Once inside the analyzer region, the ions become distributed all the way around the inner electrode as a result of the carrier gas flow and ion-ion repulsive forces. The ions are selectively transmitted within the analyzer region to an ion extraction region at an end of the analyzer region opposite the ion inlet end. In particular, a plurality of ion outlet orifices is provided around the circumference of the outer electrode for extracting the selectively transmitted ions from the ion extraction region for electrometric detection. Of course, the electrometric detectors provide a signal that is indicative of the total ion current arriving at the detector. Accordingly, the CV spectrum that is obtained using the Carnahan device does not include information relating to an identity of the selectively transmitted ions. It is a limitation of the Carnahan device that the peaks in the CV spectrum are highly susceptible to being assigned incorrectly.

Replacing the electrometric detector with a mass spectrometer detection system provides an opportunity to obtain additional experimental data relating to the identity of ions giving rise to the peaks in a CV spectrum. For instance, the mass-to-charge (m/z) ratio of ions that are selectively transmitted through the FAIMS at a particular combination of CV and DV can be measured. Additionally, replacing the mass spectrometer with a tandem mass spectrometer makes it possible to perform a full-fledged structural investigation of the selectively transmitted ions. Unfortunately, the selectively transmitted ions are difficult to extract from the analyzer region of the Carnahan device for subsequent detection by a mass spectrometer. In particular, the orifice plate of a mass spectrometer typically includes a single small sampling orifice for receiving ions for introduction into the mass spectrometer. This restriction is due to the fact that a mass spectrometer operates at a much lower pressure than the FAIMS analyzer. In general, the size of the sampling orifice into the mass spectrometer is limited by the pumping efficiency of the mass spectrometer vacuum system. In principle, it is possible to align the sampling orifice of a mass spectrometer with a single opening in the FAIMS outer electrode of the Carnahan device; however, such a combination suffers from very low ion transmission efficiency and therefore poor detection limits. In particular, the Carnahan device does not allow the selectively transmitted ions to be concentrated for extraction through the single opening. Accordingly, only a small fraction of the selectively transmitted ions are extracted from the analyzer region, the vast majority of the selectively transmitted ions being neutralized eventually upon impact with an electrode surface.

Guevremont et al. describe the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region between the cylindrical electrodes as a result of the electric fields which change with radial distance. Focusing the ions of interest has the effect of reducing the number of ions of interest that are lost as a result of the ion suffering a collision with one of the inner and outer electrodes.

In WO 00/08455, the contents of which are incorporated herein by reference, Guevremont and Purves describe an improved tandem FAIMS/MS device, including a domed-FAIMS analyzer. In particular, the domed-FAIMS analyzer includes a cylindrical inner electrode having a curved surface terminus proximate the ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, except that the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ion cloud to travel towards the ion-outlet orifice, which advantageously also prevents the ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned tandem FAIMS/MS device, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a smaller orifice leading into the vacuum system of the mass spectrometer. Accordingly, such tandem FAIMS/MS devices are highly sensitive instruments that are capable of detecting and identifying ions of interest at part-per-billion levels.

It is known that certain types of ionization sources, such as for instance an electrospray ionization source (ESI), produce ions that are highly solvated. When these highly solvated ions are introduced into the FAIMS analyzer region, some of the solvent evaporates from around the ion, thereby contaminating the carrier gas that is flowing through the analyzer region. Unfortunately, FAIMS is highly sensitive to moisture and contaminants in the gas entering the analyzer region. In fact, it is usual that contaminants, or too much water vapour, will result in complete loss of signal and failure of the FAIMS to function properly. Since electrospray ionization involves the high-voltage-assisted-atomization of a solvent mixture, the amount of water and other volatile solvents is far too high to be tolerated in the FAIMS. For this reason, the prior art ESI-FAIMS combination includes a type of solvent removal process embodied by the curtain gas, or counter-current gas flow, to prevent neutral solvent molecules from entering the FAIMS analyzer.

In WO 00/08455, the contents of which are incorporated herein by reference, Guevremont et al. teach an ESI-FAIMS combination including a small chamber disposed between and separating the FAIMS from the electrospray ionization source. The small chamber includes a gas inlet and a gas outlet, for providing a gas flow through the small chamber in a direction that is approximately transverse to the direction in which the ions are directed between the ESI and an inlet orifice of the FAIMS. A portion of the gas flow, which portion is referred to as the counter-current of gas, enters the ESI chamber so as to desolvate the ions and to carry the neutral solvent molecules away from the FAIMS and out of the ESI chamber via an outlet port thereof. Accordingly, the neutral solvent molecules are prevented from entering the vicinity of the entrance to the FAIMS. Unfortunately, the separate chamber adds to the overall complexity of the device, increases space requirements of the device, requires separate gas flow connections, and likely reduces the efficiency of introducing ions into the FAIMS since the gas flow is provided through the separate chamber in a direction that is transverse to the direction in which the ions are traveling. In a side-to-side FAIMS device, the need for a separate desolvation chamber may negate one of the advantages of the side-to-side FAIMS device, that is, a shortened distance between the ion inlet and the ion outlet of the analyzer region, which allows the side-to-side FAIMS device to be used where space considerations are particularly important.

Guevremont et al. further teach in WO 00/08455 that the counter-current of gas can be achieved by adjusting the FAIMS analyzer gas flow, so that some of the gas exits the FAIMS analyzer region through the ion inlet orifice. In this way, the introduction of neutral contaminants into the analyzer region is also avoided. Advantageously, adjusting the FAIMS analyzer gas flow may result in higher ion transmission than is achieved using a separate chamber, however, Guevremont et al. also caution that if the analyzer gas flow is adjusted accidentally, such that the gas from the ESI chamber is passed into the FAIMS analyzer region, then the performance of the FAIMS may be severely compromised for a period of time, possibly a number of hours, after the accident occurs. Furthermore, some FAIMS electrode geometries, such as for instance the side-to-side FAIMS, use a common inlet for the introducing the ions and the carrier gas into the analyzer region. Accordingly, it is not possible to adjust the FAIMS analyzer gas flow so that some of the gas exits the FAIMS analyzer region through the ion inlet orifice, as described above.

In addition, adjusting the FAIMS analyzer gas flow so that some of the gas exits the FAIMS analyzer region through the ion inlet orifice imposes an undesirable limitation upon the operational flexibility of the FAIMS. For instance, it is difficult to adjust a flow rate of the analyzer gas so as to optimize conditions for trapping ions in a domed-FAIMS analyzer when the same adjustment also affects the ion desolvation efficiency. Similarly, an optimum analyzer gas flow rate for desolvating ions may result in unacceptably rapid transmission of the ions through the analyzer region, independent of the electrode geometry, and thereby result in incomplete ion separation.

It would be advantageous to provide a compact and inexpensive system for desolvating ions for introduction into a FAIMS analyzer that overcomes the limitations of the prior art. It would be further advantageous to provide a system for desolvating ions that is adaptable for use with FAIMS devices having a plurality of different electrode geometries. Preferably, the system for desolvating ions is reliable and user friendly, so as to avoid accidental contamination of the FAIMS analyzer by neutral solvent molecules or contaminants.

SUMMARY OF THE INVENTION

In accordance with an aspect of the instant invention there is provided an apparatus for separating ions, comprising: a high field asymmetric waveform ion mobility spectrometer comprising an analyzer region defined by a space between an inner electrode and an outer electrode, the outer electrode defining an ion inlet for introducing ions into a first portion of the analyzer region and an ion outlet for extracting ions from a second portion of the analyzer region; Characterized in that: a gas-directing conduit is provided through at least a portion of one of the inner electrode and the outer electrode, the gas-directing conduit having an opening at a first end thereof for supporting fluid communication between the gas-directing conduit and the first portion of the analyzer region, the gas-directing conduit being adapted at a second end thereof opposite the first end for supporting fluid communication between a gas source and the gasdirecting conduit.

In accordance with an aspect of the instant invention there is provided an apparatus for separating ions, comprising: an inner electrode having a length and an outer surface that is curved in a direction transverse to the length, the inner electrode comprising a gas outlet within the curved outer surface and at least a gas inlet, the gas outlet being in fluid communication with the at least a gas inlet via an interior portion of the inner electrode, for introducing a flow of a gas provided through the at least a gas inlet into the analyzer region; an outer electrode having a length, a channel extending therethrough along at least a portion of the length, and a curved inner surface, the outer electrode being approximately coaxially aligned with the inner electrode, a portion of the length of the outer electrode overlapping a portion of the length of the inner electrode and forming an analyzer region therebetween, the outer electrode comprising an ion inlet within a first portion of the curved inner surface for introducing ions from an ionization source into the analyzer region and an ion outlet within a second portion of the curved inner surface for extracting ions from the analyzer region; and, an electrical controller for applying an asymmetric waveform voltage to at least one of the inner electrode and outer electrode and for applying a direct current compensation voltage to at least one of the inner electrode and outer electrode.

In accordance with another aspect of the instant invention there is provided a method for separating ions, comprising the steps of: providing a FAIMS analyzer region defined by a space between inner and outer spaced apart electrodes; producing ions at an ionization source that is in fluid communication with the analyzer region via an ion inlet within the outer electrode; introducing the ions produced at an ionization source into the FAIMS analyzer region via the ion inlet within the outer electrode; providing a flow of a gas into the analyzer region through at least a first portion of the inner electrode such that a first portion of the flow of a gas flows out of the analyzer region through the ion inlet.

BRIEF DESCRIPTION OF THE DRAWINGS

Exemplary embodiments of the invention will now be described in conjunction with the following drawings, in which similar reference numbers designate similar items:

FIG. 2b is a simplified side cross-sectional view of the inner electrode of FIG. 2a;

FIG. 2c is a simplified side cross-sectional view of another inner electrode that is suitable for use with the side-to-side FAIMS of FIG. 2a;

FIG. 2d is a simplified side cross-sectional view of still another inner electrode that is suitable for use with the side-to-side FAIMS of FIG. 2a;

FIG. 5b is a simplified side cross-sectional side view of the inner electrode of FIG. 5a;

FIG. 6b is a simplified side cross-sectional side view of the inner electrode of FIG. 6a;

DETAILED DESCRIPTION OF THE DRAWINGS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
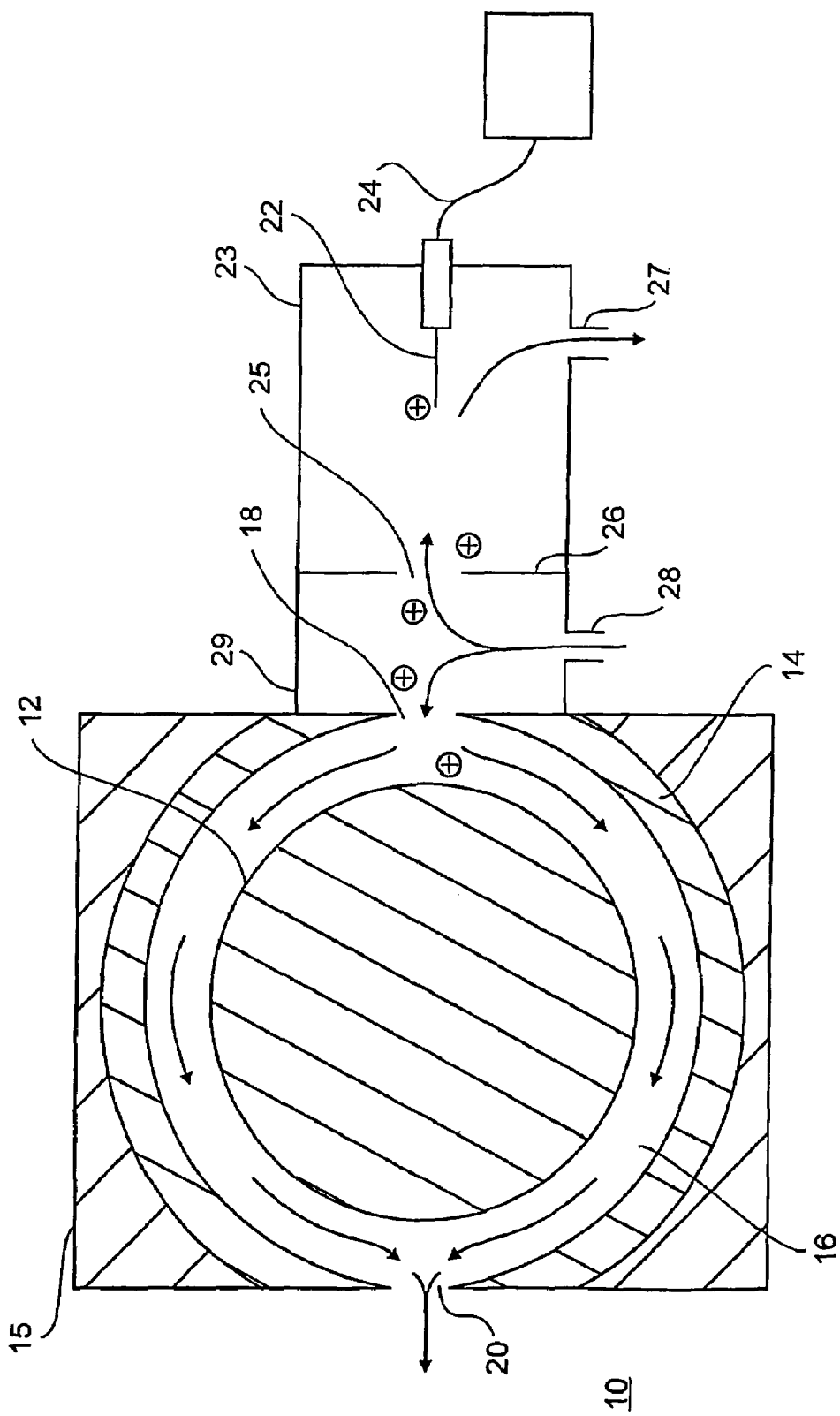
FIG. 1 is an end view of a prior art side-to-side FAIMS including a separate chamber for desolvating electrosprayed ions.

Referring to FIG. 1, shown is an end view of a prior art side-to-side FAIMS device including a separate chamber for desolvating electrosprayed ions. The side-to-side FAIMS device, shown generally at 10, includes inner and outer cylindrical electrodes 12 and 14, respectively, which are supported by an electrically insulating material 15 in an overlapping, spaced-apart arrangement. The generally annular space between the inner electrode 12 and the outer electrode 14 defines a FAIMS analyzer region 16. The analyzer region 16 is of approximately uniform width and extends around the circumference of the inner electrode 12. The inner electrode 12 is in electrical communication with a power supply (not shown) that during use is capable of applying a high voltage asymmetric waveform (DV) and a low voltage dc compensation voltage (CV) to the inner electrode 12.

An ion inlet 18 is provided through the outer electrode 14 for introducing ions from an ion source into the analyzer region 16. The ion source is in the form of an electrospray ionization ion source including a liquid delivery capillary 24 and a fine-tipped electrospray needle 22 that is held at high voltage. The electrospray needle 22 is contained within an electrospray ionization (ES) chamber 23 having a gas outlet 27. The ionization source further includes a curtain plate 26 serving as a counter-electrode for the electrospray needle 22. An orifice 25 within the curtain plate electrode 26 allows for transmission of ions produced at the electrospray needle 22 into a separate chamber 29. A flow of a gas, which is represented in FIG. 1 by a series of closed-headed arrows, is provided through a gas inlet 28 into the separate chamber 29. A first portion of the gas flows into the analyzer region 16, to carry the ions around the inner electrode 12 and toward an ion outlet 20. The orifice 25 within the curtain plate 26 allows for the flow of a second portion of the gas in a direction that is counter-current to the direction in which the ions are traveling in the separate chamber 29 towards the ion inlet 18, so as to desolvate the ions before they are introduced into the analyzer region 16. The flow of the second portion of the gas exits the ESI chamber via gas outlet 27, thereby removing the solvent vapour and preventing the contamination of the FAIMS analyzer region 16.

Once inside the FAIMS analyzer region 16, the ions are carried through an electric field that is formed within the FAIMS analyzer region 16 by the application of the DV and the CV to the inner electrode 12. Ion separation occurs within the FAIMS analyzer region 16 on the basis of the high field mobility properties of the ions. Those ions that have a stable trajectory for a particular combination of DV and CV are selectively transmitted through the FAIMS analyzer region 16, whilst other ions of the mixture collide with an electrode surface and are lost. The selectively transmitted ions are extracted from the analyzer region 16 via ion outlet 20 and are typically subjected to one of detection and further analysis.

As will be obvious to one of skill in the art, the ion inlet 18 additionally functions as a carrier gas inlet into the analyzer region 16. Accordingly, the ions and the carrier gas are co-introduced into a prior art side-to-side FAIMS, and travel in a same direction through the analyzer region 16 toward the ion outlet 20. Since no separate carrier gas inlet is provided into a prior art side-to-side FAIMS, it is not possible to direct a flow of gas counter-current to the direction the ions are traveling in the vicinity of the ion inlet 18. As a consequence, providing the separate chamber 29 to support desolvation of the ions before they are introduced into the analyzer region of a side-to-side FAIMS is critically important to the operaion of the electrospray ionization source when used in conjunction with a FAIMS analyzer.

Figure 2A:
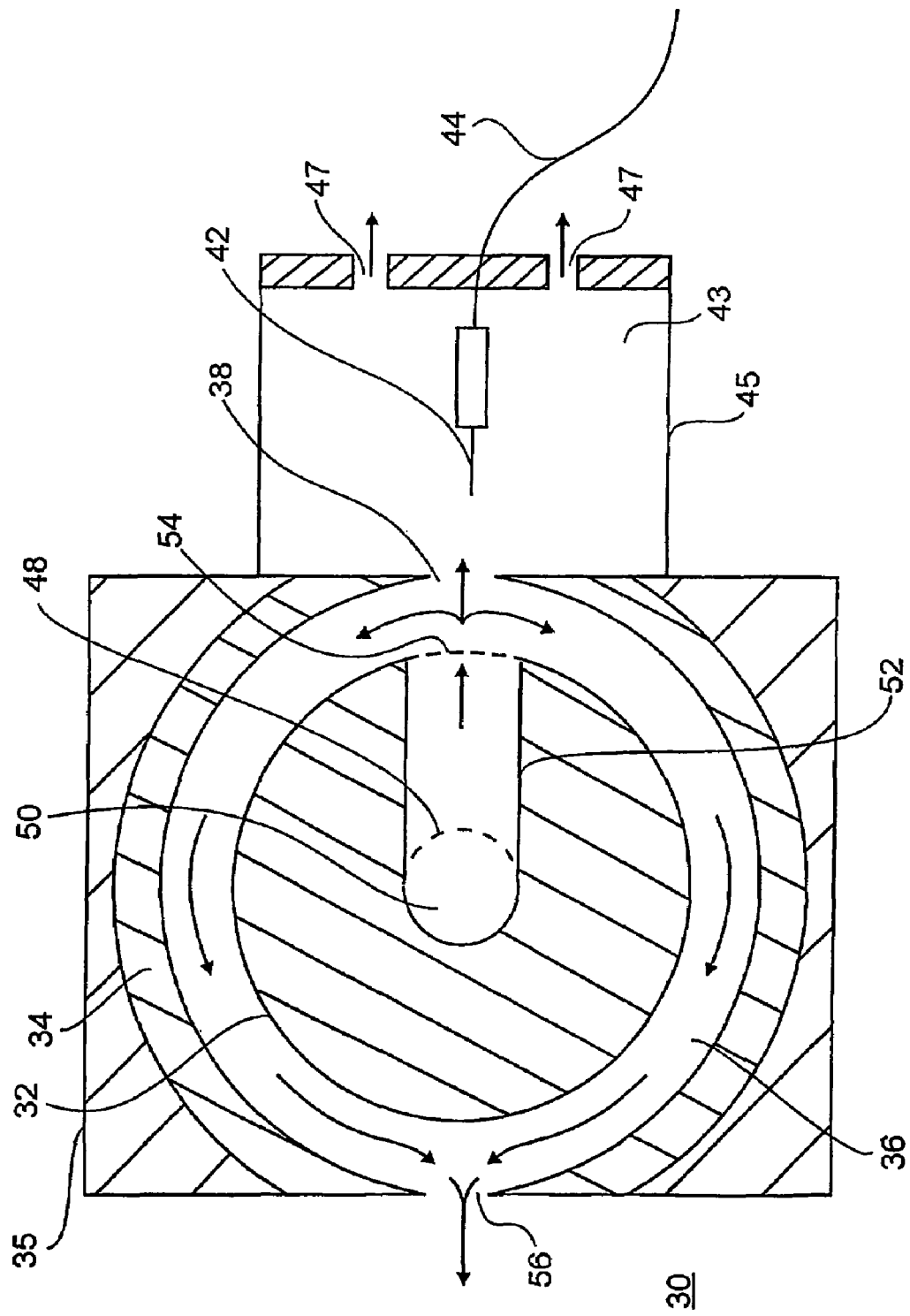
FIG. 2a is an end view of a side-to-side FAIMS including an inner electrode having a gas directing conduit according to the instant invention.

Referring now to FIG. 2a, shown is an end view of a side-to-side FAIMS including an inner electrode having a gas-directing conduit, such as for instance a bored-out channel, according to the instant invention. The side-to-side FAIMS device, shown generally at 30, includes inner and outer cylindrical electrodes 32 and 34, respectively, which are supported by an electrically insulating material 35 in an overlapping, spaced-apart arrangement The generally annular space between the inner electrode 32 and the outer electrode 34 defines a FAIMS analyzer region 36. The analyzer region 36 is of approximately uniform width and extends around the circumference of the inner electrode 32. The inner electrode 32 is in electrical communication with a power supply (not shown) that during use is capable of applying a high voltage asymmetric waveform voltage (DV) and a low voltage dc compensation voltage (CV) to the inner FAIMS electrode 32.

An ion inlet 38 is provided through the outer electrode 34 for introducing ions from an ion source into the analyzer region 36. The ion source is in the form of an electrospray ionization (ESI) source including a liquid delivery capillary 44 and a fine-tipped electrospray needle 42 that is held at high voltage. An optional ionization cylinder 45 is sealed gas tight against the insulating material 35 to define an ESI chamber 43 that contains the electrospray needle 42. The ionization cylinder 45 includes at least a gas outlet 47 for allowing gas to exit from the ESI chamber 43. The ionization cylinder 45, when present, is optionally fabricated from one of an insulating material and a conductive material. If the ionization cylinder 45 is conductive, it is optionally in electrical communication with the outer electrode 34. Of course, the ionization cylinder 45 is sufficiently large such that it does not have an adverse effect on the electrospray ionization process, for example as a result of an electrical discharge between the tip of the electrospray needle 42 and the ionization cylinder 45.

Figure 2B:
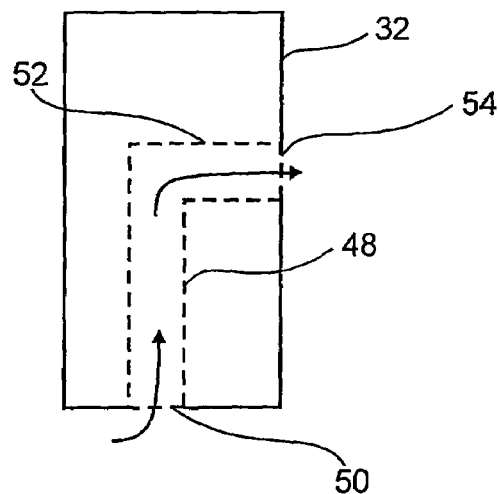

Referring still to FIG. 2a, the ESI chamber is provided in direct fluid communication with the analyzer region 36. In particular, a separate chamber similar to drawing element 29 of FIG. 1 is absent in the FAIMS device that is shown generally at 30 in FIG. 2a. Accordingly, the outer electrode 34 serves as the counter-electrode of the electrospray source. Some of the ions that are produced by the electrospray needle 42 pass through the ion inlet 38 and into the analyzer region 36. However, the neutral solvent vapour cannot enter the analyzer region 36. This is made possible by the dual functionality of the inner electrode 32. As was described with reference to FIG. 1, the asymmetric waveform is preferentially applied to the inner electrode 32. In addition, a conduit 48 is provided through the core of the inner electrode 32 to support passage of a flow of a gas through the inner electrode 32 and into the analyzer region 36. To this end, an outlet 52 is provided between the conduit 48 and the analyzer region 36 for directing the flow of gas from the conduit 48 through an opening 54 within the surface of the inner electrode 32, and finally into the analyzer region 36. For instance, the outlet 52 is a hole that is drilled approximately radially into the inner electrode 32 and that is in fluid communication with the conduit 48, as is shown in FIG. 2b. Preferably, the opening 54 of the outlet 52 in the inner electrode 32 is sufficiently large to prevent a high velocity, high turbulence gas flow, which could adversely affect the efficiency of ion transport into the FAIMS analyzer region 36.

During use, gas is introduced into the port 50 from a not illustrated gas source. The gas flows longitudinally within the conduit 48 through the inner electrode 32, is diverted through the outlet 52, passes out of the inner electrode 32 via the opening 54, and enters into the FAIMS analyzer region 36 in the vicinity of the ion inlet 38. As is shown schematically by the closed-headed arrows in FIG. 2a, if the volume of gas introduced through the conduit 48 in the inner electrode 32 exceeds the volume of gas flowing out of the analyzer region 36 through an ion outlet 56, then the gas will split into two flows comprising a desolvation gas and a carrier gas. The desolvation gas flows through the ion inlet 38 in a direction counter-current to the direction the ions are traveling, continuing toward the electrospray needle 42 in the ESI chamber 43, and eventually exiting the ESI chamber 43 via one of the gas outlets 47. The carrier gas flows approximately equally around each side of the inner electrode 32, and out through the ion outlet 56, as is illustrated by the arrows in FIG. 2a.

Advantageously, the high voltage that is applied to the ionization source results in a strong electric field that directs electrosprayed ions away from the electrospray needle 42 and toward the counter-electrode, in this instance the outer electrode. Some of the ions enter the analyzer region 36 through the ion inlet 38, through the countercurrent desolvation gas flow, and into the carrier gas flow stream that transports ions through the analyzer region 36 to the ion outlet 56. The dc voltage difference between the inner electrode 32 and the outer electrode 34, in other words the CV, acts to pull the ions through the ion inlet 38 into the analyzer region 36. Of course, the electric fields on either side of the ion inlet 38 penetrate through the inlet and add to the field on the other side of the ion inlet 38. The desolvation gas that flows toward the electrospray needle 42 through the ion inlet 38 aids in desolvation and prevents solvent and other neutrals from entering the ion inlet 38. Further advantageously, the electrosprayed ions are desolvated without the need for a separate desolvation chamber, thereby allowing a more efficient transfer of ions into the FAIMS device 30.

Preferably, the ion inlet 38 is sufficiently large that the fields from the ionization region are able to penetrate through the ion inlet 38, so as to assist the travel of the ions through the countercurrent gas flow, or desolvation gas, and into the analyzer region where the ions become entrained in the carrier gas flow that transports the ions through the analyzer region 36 to the ion outlet 56. Optionally, at least one of the ion inlet 38 and the ion outlet 56 is provided as a slit-shaped opening in the outer electrode 34.

Figure 2C:
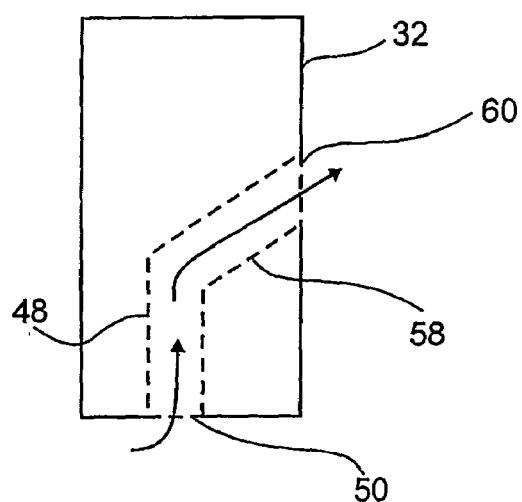
Figure 2D:
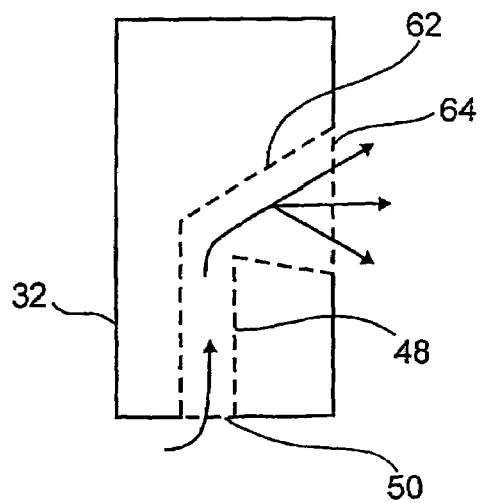

In the embodiment that is described with reference to FIGS. 2a and 2b, the conduit 48 is aligned generally along the longitudinal axis of the inner electrode 32, intersecting the outlet 52 at right angles. Of course, other configurations of the conduit/outlet may also be envisaged. Referring now to FIG. 2c, shown is a first optional configuration in which the conduit 48 and an outlet 58 intersect at other than right angles. In particular, the outlet 58 is angled upwardly in the figure, so as to direct in a predetermined direction a flow of gas through an opening 60 of the outlet 58. Referring now to FIG. 2d, shown is a second optional configuration in which the conduit 48 intersects a funnel shaped outlet 62, which enlarges in a direction that is generally radially away from the longitudinal axis of the inner electrode. Accordingly, a gas flow through the conduit 48 enlarges as it moves through the outlet 62, such that the gas flow rate decreases and the gas flow spreads out through the opening 64 into a larger portion of the analyzer region near the ion inlet 38. Of course, the opening 64 affects the electric fields in an adjacent portion of the analyzer region. Accordingly, the size of the opening 64 is selected so as not to negatively affect the performance of the FAIMS analyzer.

Optionally, the conduit 48 is disposed other than generally along the longitudinal axis of the inner electrode 32, or even at an angle to the longitudinal axis. Further optionally, the conduit 48 includes a not illustrated plurality of gas inlets, each gas inlet of the plurality of gas inlets in communication with a source of a different gas.

Figure 3:
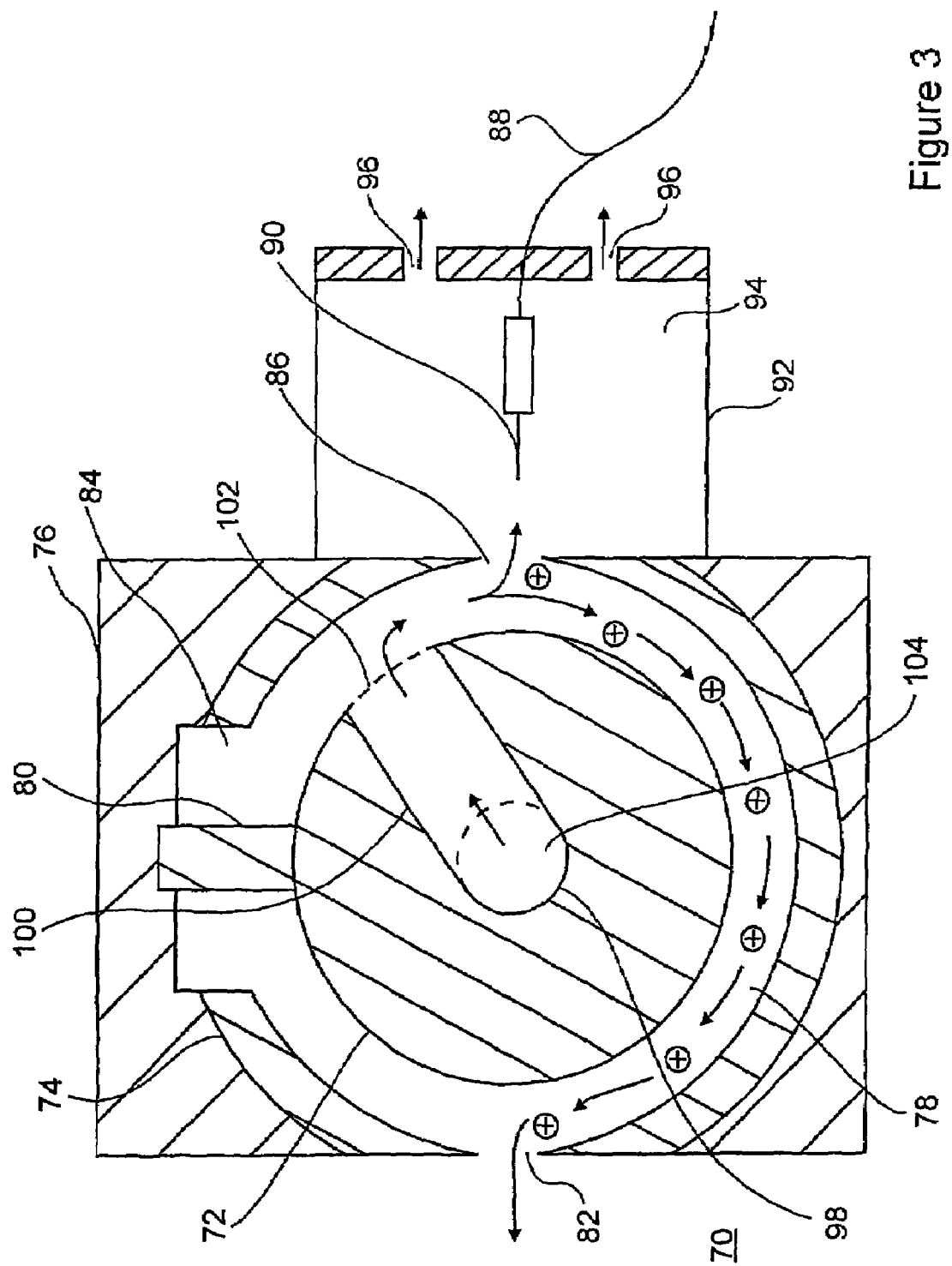
FIG. 3 is an end view of another side-to-side FAIMS including an inner electrode having a gas directing conduit according to the instant invention.

Referring now to FIG. 3, shown is an end view of another side-to-side FAIMS including an inner electrode having a gas-directing conduit, such as for instance a bored-out channel, according to the instant invention. The side-to-side FAIMS device, shown generally at 70, includes inner and outer generally cylindrical electrodes 72 and 74, respectively, which are supported by an electrically insulating material 76 in an overlapping, spaced-apart arrangement. The inner electrode 72 is in electrical communication with a power supply (not shown) that during use is capable of applying a high voltage asymmetric waveform (DV) and a low voltage dc compensation voltage (CV) to the inner electrode 72.

The generally annular space between the inner electrode 72 and the outer electrode 74 defines a FAIMS analyzer region 78. In the device 70, the inner electrode 72 is modified so that a protruding part 80 of the inner electrode 72 forms a gas tight seal with the electrically insulating material 76, thereby forcing the gas flow, which is represented in the figure by a series of closed headed arrows, around one side of the inner electrode 72 toward an ion outlet 82. Optionally, the protruding part 80 of the inner electrode 72 is replaced by a protruding section of the electrically insulating material 76, which extends radially inwardly toward the inner electrode 72. When a protruding section of the electrically insulating material 76 is used to control the direction of gas flows around the circumference of the inner electrode 72, the size of an opening 84 in the outer electrode 74 is optionally reduced, since the electrically insulating material 76 does not readily support an electrical discharge. Preferably, however, the design of a protruding section that is fabricated from the electrically insulating material 76 must avoid, or at least minimize, the occurrences of electrical discharge and the subsequent creation of burn tracks in the electrically insulating material.

An ion inlet 86 is provided through the outer electrode 74 for introducing ions from an ion source into the analyzer region 78. The ion source is in the form of an electrospray ionization (ESI) source including a liquid delivery capillary 88 and a fine-tipped electrospray needle 90 that is held at high voltage. An optional ionization cylinder 92 is sealed gas tight against the insulating material 76 to define an ESI chamber 94 that contains the electrospray needle 90. The ionization cylinder 92 includes at least a gas outlet 96 for allowing gas to exit from the ESI chamber 94. The ionization cylinder 92, when present, is optionally fabricated from one of an insulating material and a conductive material. If the ionization cylinder 92 is conductive, it is optionally in electrical communication with the outer electrode 74. Of course, the ionization cylinder 92 is sufficiently large such that it does not have an adverse effect on the electrospray ionization process, for example as a result of an electrical discharge between the tip of the electrospray needle 90 and the ionization cylinder 92.

Referring still to FIG. 3, the ESI chamber 94 is provided in direct fluid communication with the analyzer region 78. In particular, a separate chamber similar to drawing element 29 of FIG. 1 is absent in the FAIMS device that is shown generally at 70 in FIG. 3. Accordingly, the outer electrode 74 serves as the counter-electrode of the electrospray source. Some of the ions that are produced by the electrospray needle 90 pass through the ion inlet 86 and into the analyzer region 78. However, the neutral solvent vapour cannot enter the analyzer region 78. This is made possible by the dual functionality of the inner electrode 72. As was described with reference to FIG. 1, the asymmetric waveform is preferably applied to the inner electrode 72. In addition, a conduit 98 is provided through the core of the inner electrode 72 to support passage of a flow of a gas through the inner electrode 72 and into the analyzer region 78. To this end, an outlet 100 is provided between the conduit 98 and the analyzer region 78 for directing the flow of gas from the conduit 98 through an opening 102 within the surface of the inner electrode 72, and finally into the analyzer region 78. For instance, the outlet 100 is a hole that is drilled approximately radially into the inner electrode 72 and that is in fluid communication with the conduit 98. Preferably, the opening 102 of the outlet 100 in the inner electrode 72 is sufficiently large to prevent a high velocity, high turbulence gas flow, which could adversely affect the efficiency of ion transport into the FAIMS analyzer region 78.

During use, gas from a not illustrated gas source is introduced via a port 104 into the conduit 98. The gas flows longitudinally within the conduit 98 through the inner electrode 72, is diverted through the outlet 100, passes out of the inner electrode 72 via the opening 102, and enters into the FAIMS analyzer region 78. As is shown schematically by the closed-headed arrows in FIG. 3, if the volume of gas that is introduced through the conduit 98 in the inner electrode 72 exceeds the volume of gas flowing out of the analyzer region 78 through the ion outlet 82, then the gas will split into two flows comprising a desolvation gas and a carrier gas. The desolvation gas flows through the ion inlet 86 in a direction counter-current to the direction the ions are traveling, continuing toward the electrospray needle 90 in the ESI chamber 94, and eventually exiting the ESI chamber 94 via one of the gas outlets 96. The carrier gas flows in one direction only around the circumference of the inner electrode 72, being blocked in the other direction by the protruding part 80. The carrier gas flowing in the one direction exits the analyzer region via the ion outlet 82.

The location around the circumference of the inner electrode 72 at which the gas emerges from the opening 102 and enters the analyzer region 78 is a critical consideration. In the device 70, the opening 102 is located, in a circumferential direction, between the ion inlet 86 and the protruding part 80. Such an arrangement provides a gas flow exiting the analyzer region 78 through the ion inlet 86 that is suitable for desolvating the ions produced at the electrospray needle 90 and another gas flow for carrying the desolvated ions through the analyzer region toward the ion outlet 82. Optionally, the opening 102 is positioned approximately facing the ion inlet 86, such that gas flows are created similar to the ones that were described with reference to FIG. 2a. Of course, the carrier gas flow in the device 70 travels in one direction only around the inner electrode 72, being blocked in the other direction by the protruding part 80. Conversely, a device that is similar to the one shown generally at 70, but in which the opening 102 in the inner electrode 72 is positioned, in a circumferential direction, between the ion inlet 86 and the ion outlet 82, is expected to fail. This device is expected to fail because the electric fields that are produced by the ionization source do not extend far enough into the analyzer region 78 to carry an ion through the countercurrent gas flow, such as for example around the inner electrode 72 to a point that is beyond the opening 102, and into a portion of the gas stream that transports ions in the direction of the ion outlet 82.

Optionally, when a protruding section of the electrically insulating material 76 is used to control the direction of gas flows around the circumference of the inner electrode 72, the inner electrode 72 optionally is rotatable about it longitudinal axis. For example, the inner electrode 72 may be rotated through a limited range of positions relative to the outer electrode 74, for optimizing the location of the opening 102 relative to the ion inlet 86.

Figure 4A:
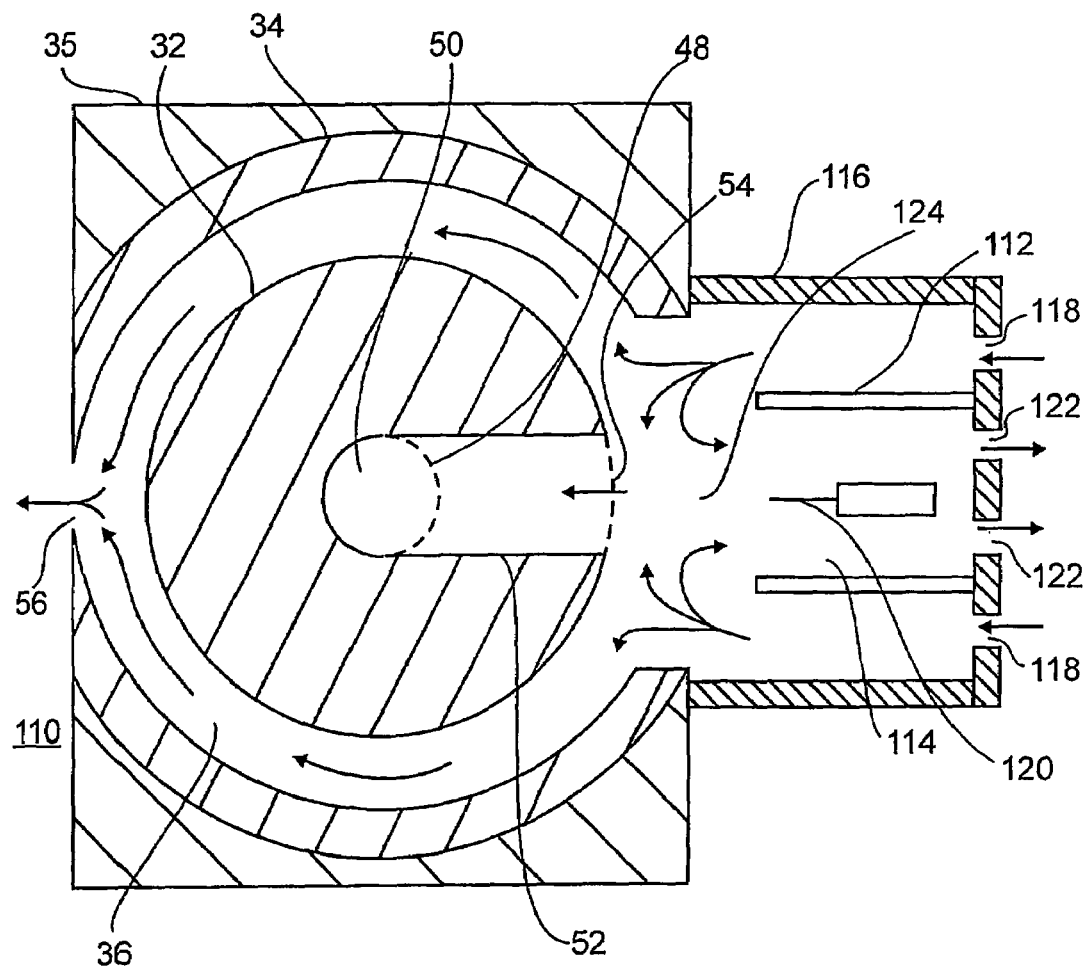
FIG. 4a is an end view of still another side-to-side FAIMS including an inner electrode having a gas directing conduit according to the instant invention, showing gas flows during a first mode of operation.
Figure 4B:
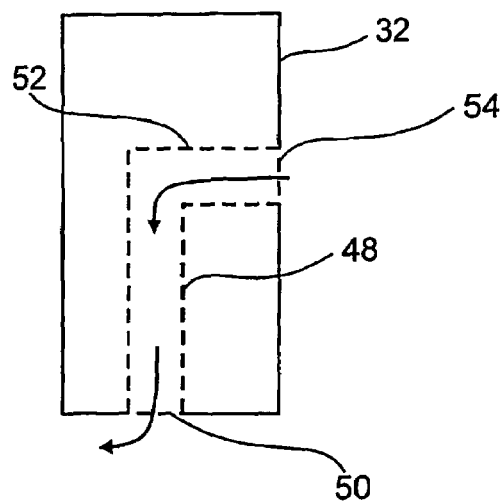
FIG. 4b is a simplified side cross-sectional view of the inner electrode of FIG. 4a, showing gas flows during the first mode of operation.

Referring now to FIG. 4a, shown is an end view of still another side-to-side FAIMS including an inner electrode having a gas-directing conduit according to the instant invention, and showing gas flows produced during a first mode of operation. Elements labeled with the same numerals have the same function as those illustrated in FIG. 2a. The ESI chamber of this embodiment is modified relative to that shown in FIG. 2a. The ionization cylinder 112 within the ESI chamber 114 does not make a gas tight seal against the FAIMS device. Instead, the conductive ionization cylinder 112 is enclosed within a housing 116 that is secured gas tight against the electrically insulating material 35 of the FAIMS device 110. At least a gas inlet 118, two gas inlets 118 being shown in FIG. 4a, are provided through the housing 116 at locations for introducing a gas into the space between the ionization cylinder 112 and the housing 116. As is illustrated in FIG. 4a by the series of closed-headed arrows, the introduced gas splits into three approximately separate flows on exiting the space between the ionization cylinder 112 and the housing 116. Referring now to FIG. 4b, a first flow, for instance the sample gas, travels through conduit 48 within the inner electrode 32 and exits through a port 50 in one of the flat end-surfaces of the inner electrode 32. Referring again to FIG. 4a, a second gas flow, for instance the desolvation gas, travels toward an ESI needle 120, and out through at least one gas outlet 122 from the ionization chamber 114. A third gas flow, for instance the carrier gas, travels around both sides of the inner electrode 32 and toward the ion outlet 56. As was described with reference to FIG. 2a, the electric fields from the ionization source assist in transporting ions through the countercurrent gas flow, and into the carrier gas flow that transports the ions to the ion outlet 56.

Optionally, the gas flow is controlled by adding a valve and a small pump to the port 50 in the inner electrode and/or to the gas outlets 122 in the ionization chamber 114. Further optionally, the gas flow in the configuration that is shown in FIG. 4a is changed so that the sample gas flow is eliminated and instead gas is introduced to the FAIMS device through both the conduit 48 in the inner electrode 32 and through the gas inlets 118 in the housing 116.

Figure 4C:
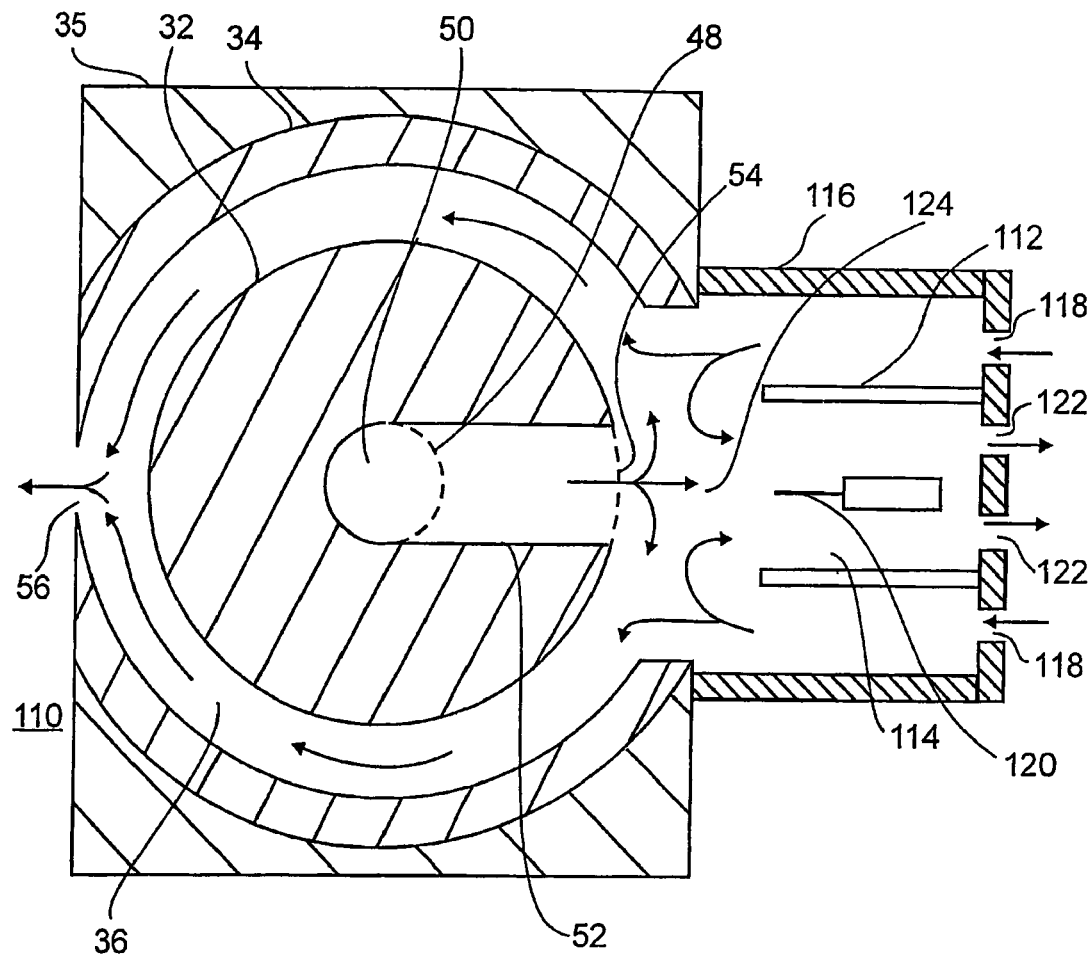
FIG. 4c is an end view of the side-to-side FAIMS shown at FIG. 4a, showing gas flows during a second mode of operation.
Figure 4D:
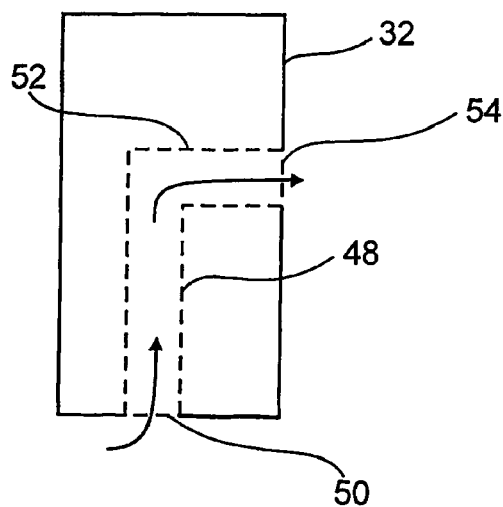
FIG. 4d is a simplified side cross-sectional view of the inner electrode of FIG. 4b, showing gas flows during the second mode of operation.

Referring now to FIG. 4c, shown is an end view of the side-to-side FAIMS shown at FIG. 4a, showing gas flows produced during a second mode of operation. Elements labeled with the same numerals have the same function as those illustrated in FIGS. 2a and 4a When operating in the second mode, gas entering through the gas inlets 118 in the housing 116 splits into first and second approximately separate flows, as is illustrated by the series of closed-headed arrows in the figure. The first flow travels in a direction toward the electrospray needle 120 and exits through the gas outlets 122 in the ionization chamber 114, thereby making up a portion of a total desolvation gas flow. The second flow travels through the ion inlet 124 and around both sides of the inner electrode 32 toward the ion outlet 56, thereby making up a portion of the total carrier gas flow. Now referring also to FIG. 4d, gas entering through the conduit 48 in the inner electrode 32 splits into third and fourth approximately separate flows, as shown by the series of closed-headed arrows in FIGS. 4c and 4d. The third flow travels through the ion inlet 124 in a direction toward the electrospray needle 120 and exits through the gas outlets 122 in the ionization chamber 114, thereby making up a remaining portion of a total desolvation gas flow. Similarly, the fourth flow travels through the analyzer region around both sides of the inner electrode 32 toward the ion outlet 56, thereby making up a remaining portion of the total carrier gas flow. As was described with reference to FIG. 2a and FIG. 4a, the electric fields from the ionization source assist in transporting ions through the countercurrent gas flow, and into the carrier gas flow that transports the ions to the ion outlet 56.

Figure 5A:
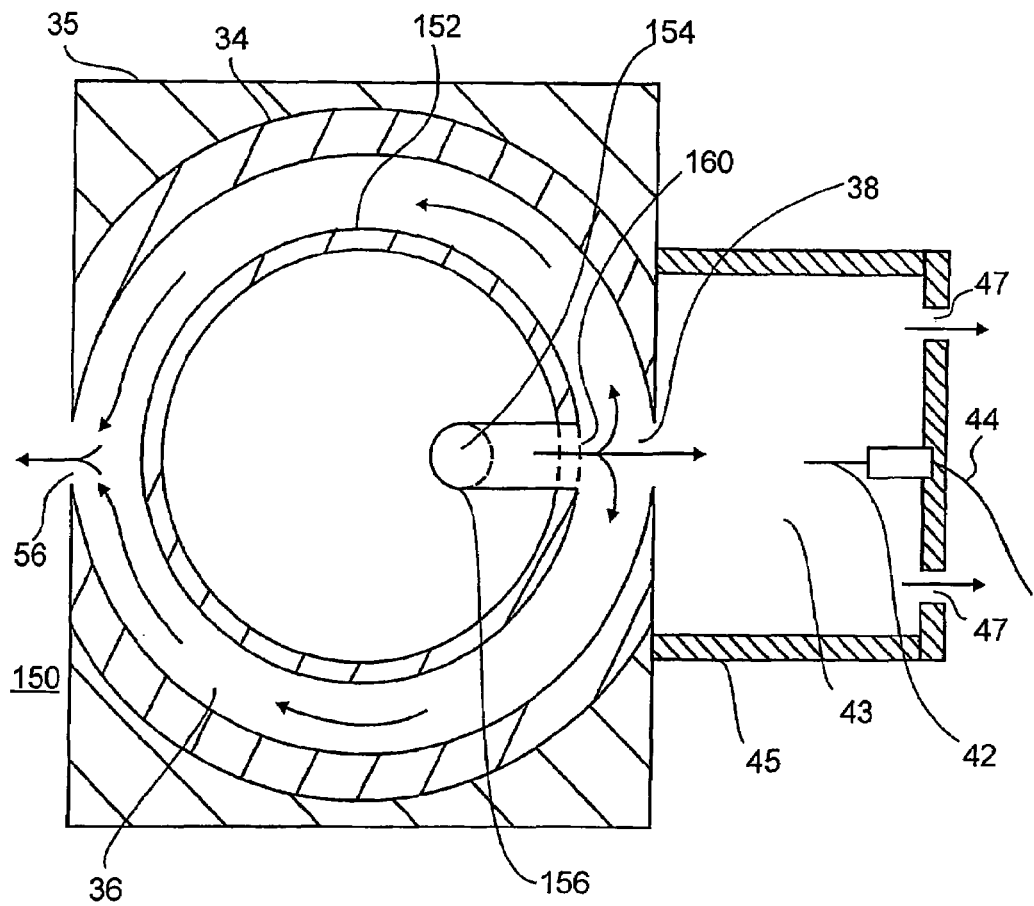
FIG. 5a is an end view of yet another side-to-side FAIMS including a tubular inner electrode containing a separate gas directing tube according to the instant invention.
Figure 5B:
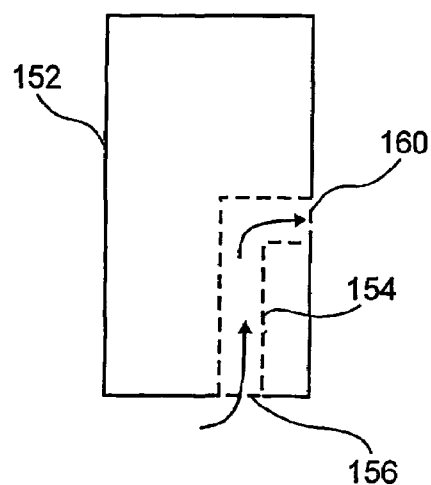

Referring now to FIG. 5a, shown is an end view of yet another side-to-side FAIMS according to the instant invention. Elements labeled with the same numerals have the same function as those illustrated in FIG. 2a. Unlike the device 30 that was described with reference to FIGS. 2a and 2b, the device shown generally at 150 includes a tubular inner electrode 152 containing a gas-directing conduit in the form of a separate tube 154. Now referring also to FIG. 5b, the tube 154 is disposed inside the tubular inner electrode 152. Preferably, the tube 154 forms a gas tight seal with an inner surface of the tubular inner electrode 152 about an opening 160 through the tubular inner electrode 152. The tube 154 is also preferably supported by a gas delivery system at a port 156 of the tube 154. Gas entering the tube 154 through the port 156 emerges into the analyzer region 36 via the opening 160. The gas flow splits into a first portion flowing through the analyzer region 36 and a second portion flowing through the ionization chamber 43 as indicated in the figure by the series of closed-headed arrows, are as described supra with reference to FIG. 2a. Optionally, the tube 154 is flexibly mounted within the tubular inner electrode 152, such that a free length of the tube 154 is adjustable. Preferably, adjusting the free length of the tube 154 varies the angle of gas introduction into the analyzer region.

Figure 6A:
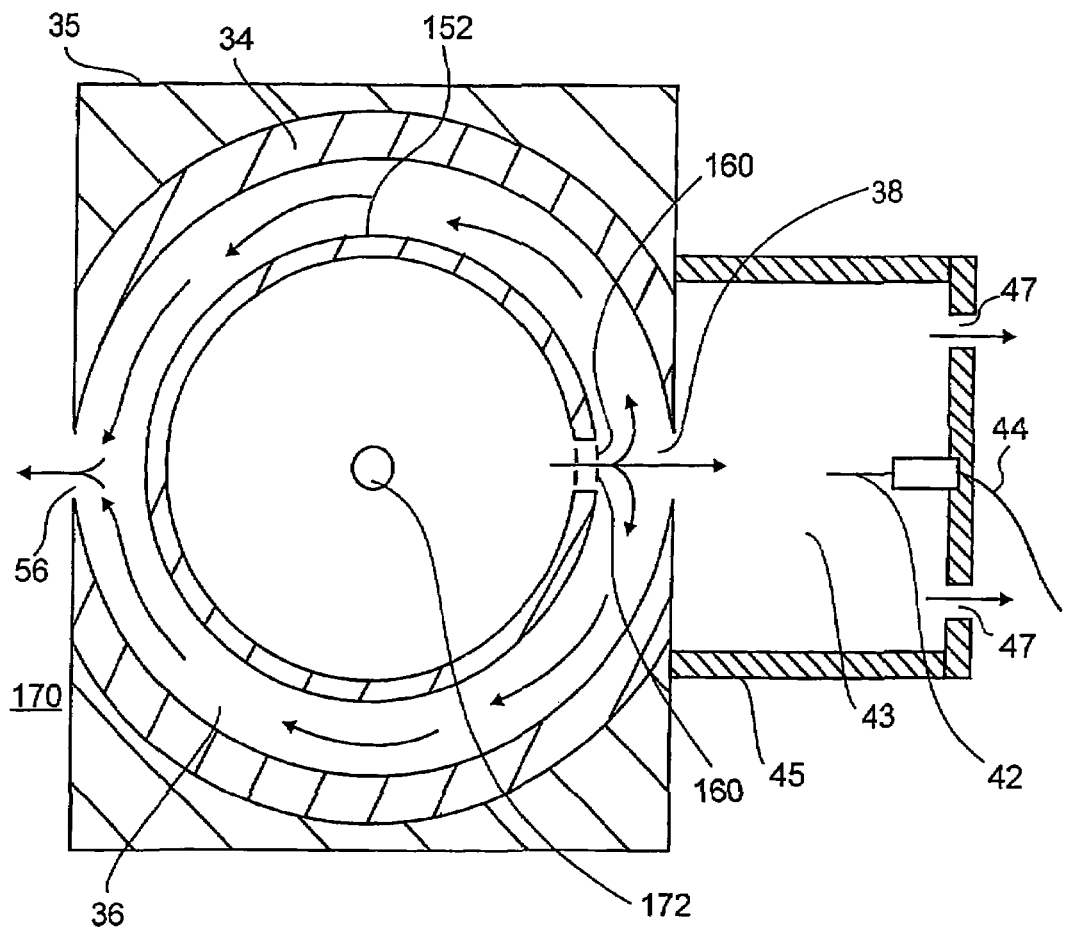
FIG. 6a is an end view of yet another side-to-side FAIMS including a tubular inner electrode, absent a separate gas directing tube, according to the instant invention.
Figure 6B:
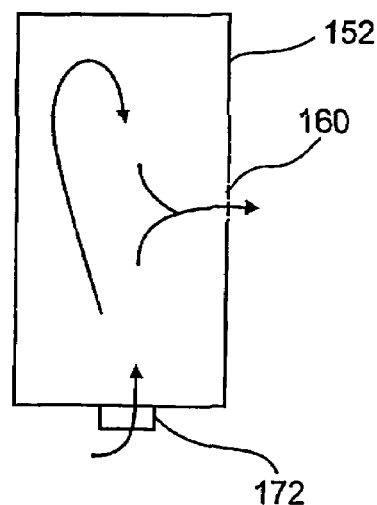

Referring now to FIG. 6a, shown is an end view of yet another side-to-side FAIMS according to the instant invention. Elements labeled with the same numerals have the same function as those illustrated in FIG. 5a. Unlike the device 150 that was described with reference to FIGS. 5a and 5b, the device shown generally at 170 includes a tubular inner electrode 152 having endfaces, which functions as a gas-directing conduit, absent a separate tube or a bored-through channel. Referring now also to FIG. 6b, a port 172 is provided at one of the endfaces of the tubular inner electrode 152. The tubular inner electrode 152 is sealed gas tight except for the opening 160. Gas entering the interior volume of the tubular inner electrode 152 through the port 172 emerges into the analyzer region 36 via the opening 160. The gas flow splits into a first portion flowing through the analyzer region 36 and a second portion flowing through the ionization chamber 43 as indicated in the figure by the series of closed-headed arrows, are as described supra with reference to FIG. 2a.

Figure 7:
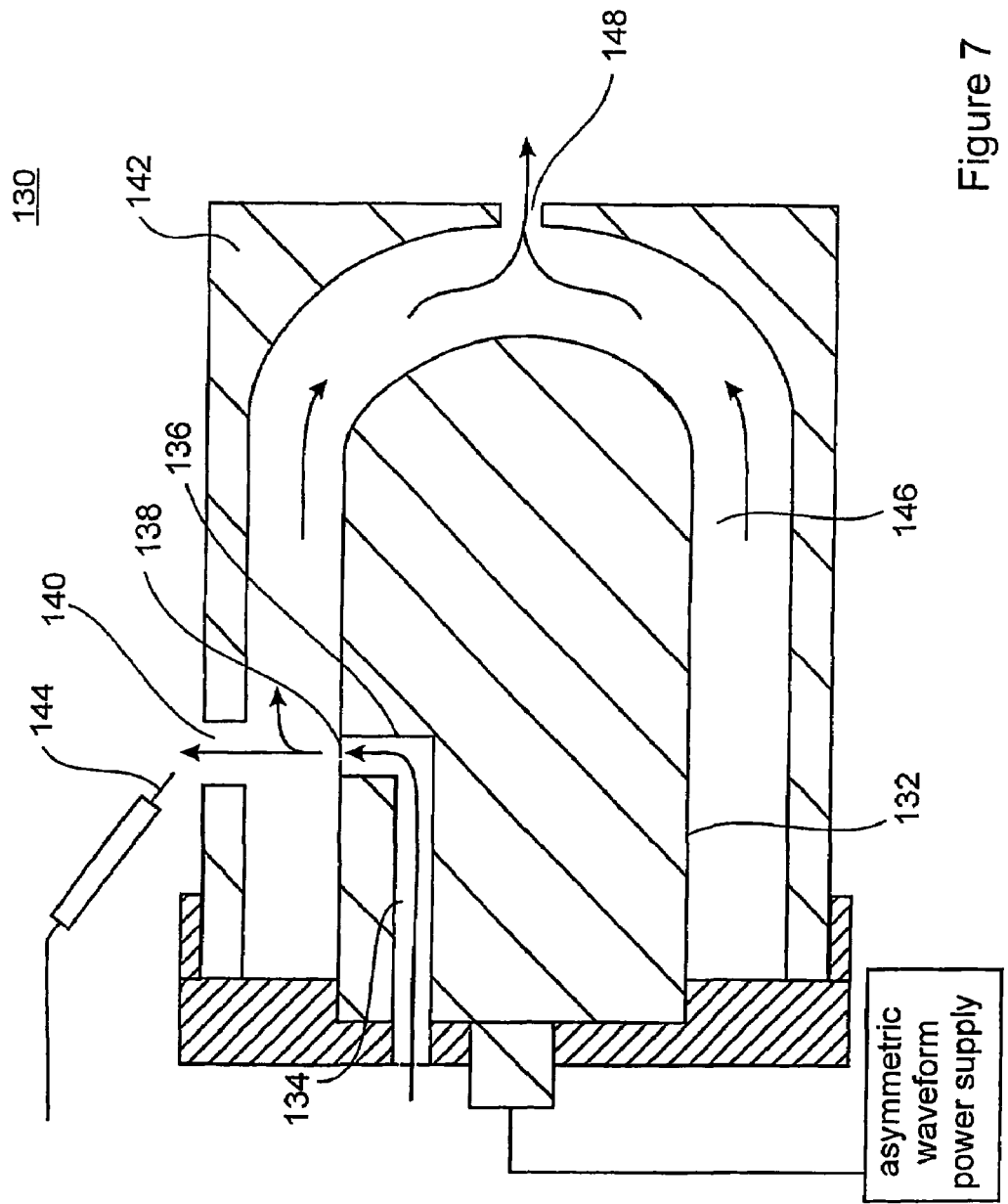
FIG. 7 is a simplified block diagram of a domed-FAIMS analyzer including an inner electrode having a gas-directing conduit according to the instant invention; and, FIG. 8 is a simplified flow diagram for a method of separating ions according to the instant invention.

The detailed description of the instant invention is provided in terms of a specific and non-limiting example of a particular FAIMS electrode geometry, specifically a cylindrical side-to-side FAIMS electrode geometry. Of course, the inventors also envisage alternative embodiments of the instant invention, which encompass other FAIMS electrode geometries. Referring now to FIG. 7, shown is a simplified block diagram of one such alternative embodiment, comprising a domed-FAIMS analyzer 130 including an inner electrode 132 having a gas-directing conduit 134 according to the instant invention. Preferably, the gas-directing conduit 134 intersects an outlet 136, such that an opening 138 of the outlet 136 is disposed opposite an ion inlet 140 within an outer electrode 142. If the volume of gas introduced through the conduit 134 in the inner electrode 132 exceeds the volume of gas flowing out of an analyzer region 146 through an ion outlet 148, then the volume of introduced gas will split into two approximately separate gas flows, comprising a desolvation gas and a carrier gas, as shown by the series of closed-headed arrows in the figure. The desolvation gas flows outwardly from the analyzer region 146 through the ion inlet 140 in a direction that is counter-current to the electrosprayed ions, thereby assisting the desolvation of the ions. The carrier gas flows along the analyzer region in the generally annular space between the inner and outer electrodes, 132 and 142, respectively, and out through the ion outlet 148. Advantageously, the electrosprayed ions are desolvated absent an external desolvation chamber, or curtain plate assembly.

Figure 8:
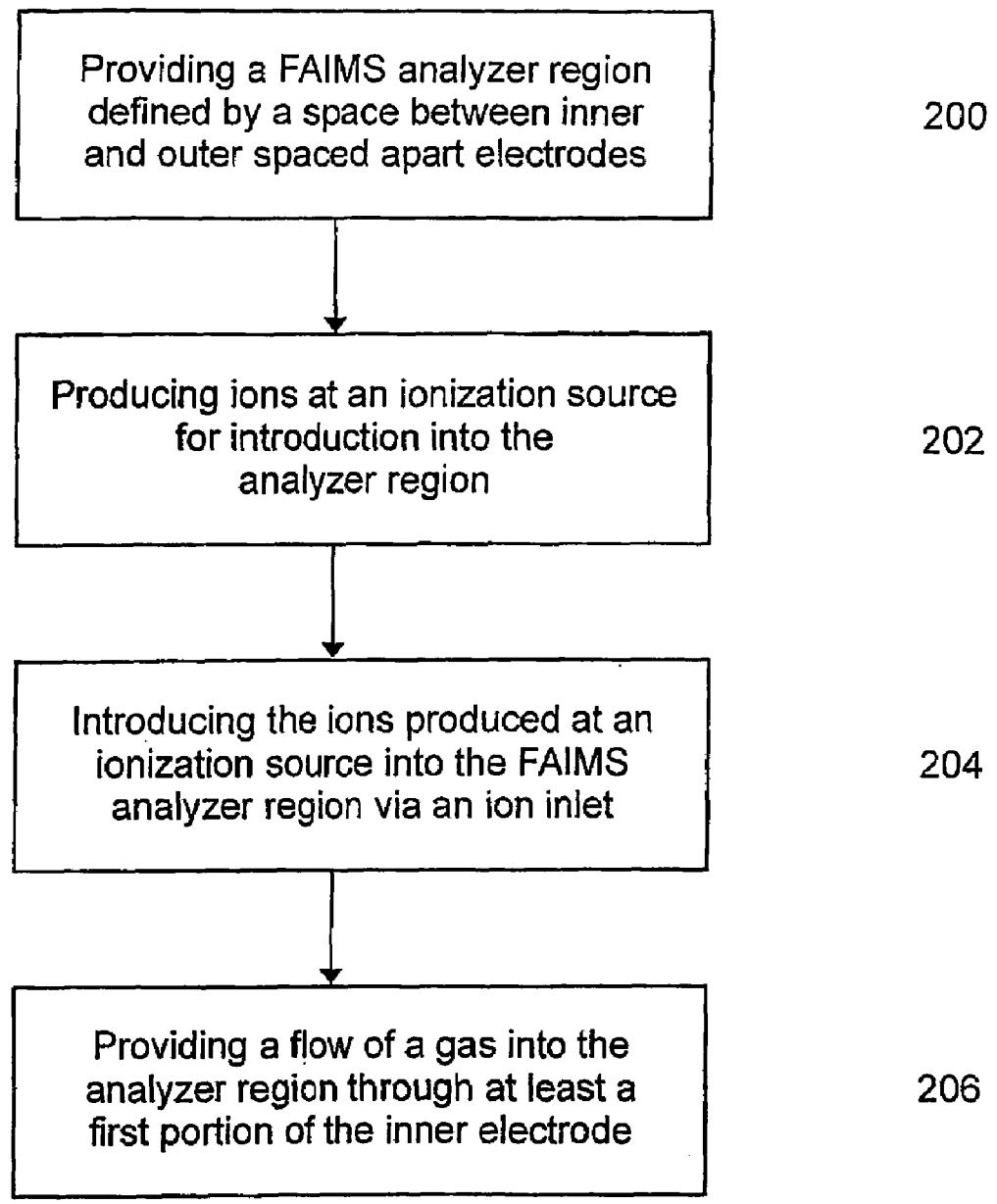

Referring now to FIG. 8, shown is a simplified flow diagram of a method for separating ions according to the instant invention. At step 200, a FAIMS analyzer region is provided, the FAIMS analyzer region being defined by a space between inner and outer spaced apart electrodes. At step 202, ions are produced at an ionization source for introduction into the analyzer region. In particular, the ionization source is an electrospray ionization source for producing ions from a sample in a liquid state, such that the produced ions are solvated. At step 204, the ions are introduced into the FAIMS analyzer region. In particular, the electric field from the ionization source extends through an ion inlet and into the FAIMS analyzer region, which directs the ions away from the ionization source and toward the counter electrode, in this case the outer electrode, and thereby assists in transporting ions into the analyzer region. At step 206, a flow of a gas is provided through an interior portion of the inner eletrode and into the analyzer region, such that a first portion of the flow of a gas flows out of the analyzer region through the ion inlet and counter-current to a direction that ions are traveling in the vicinity of the ion inlet. Advantageously, the counter-current of gas, or desolvation gas, acts to desolvate the ions that are being directed toward the ion inlet by the electric fields from the ionization source. Accordingly, the ions are approximately desolvated by the time the ions enter the FAIMS analyzer region. Preferably, the ions are desolvated to at least an extent that supports proper operation of the FAIMS.

Figure 9A:
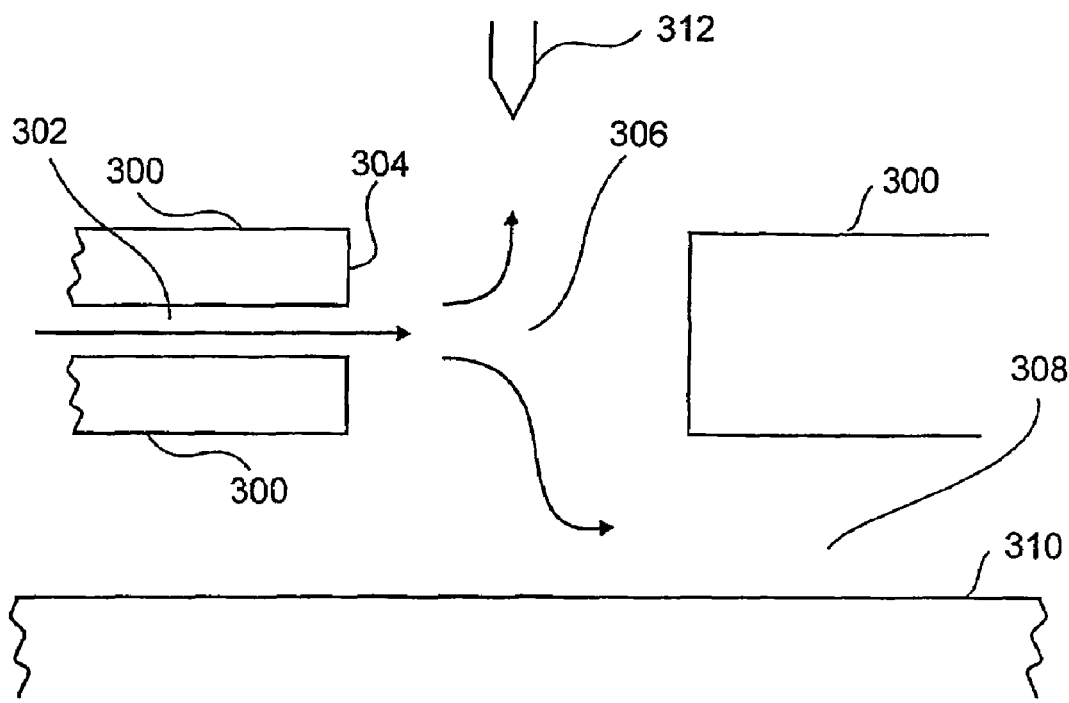
FIG. 9a is a partial cross sectional view of a domed-FAIMS apparatus including an outer electrode having a gas-directing conduit according to the instant invention.
Figure 9B:
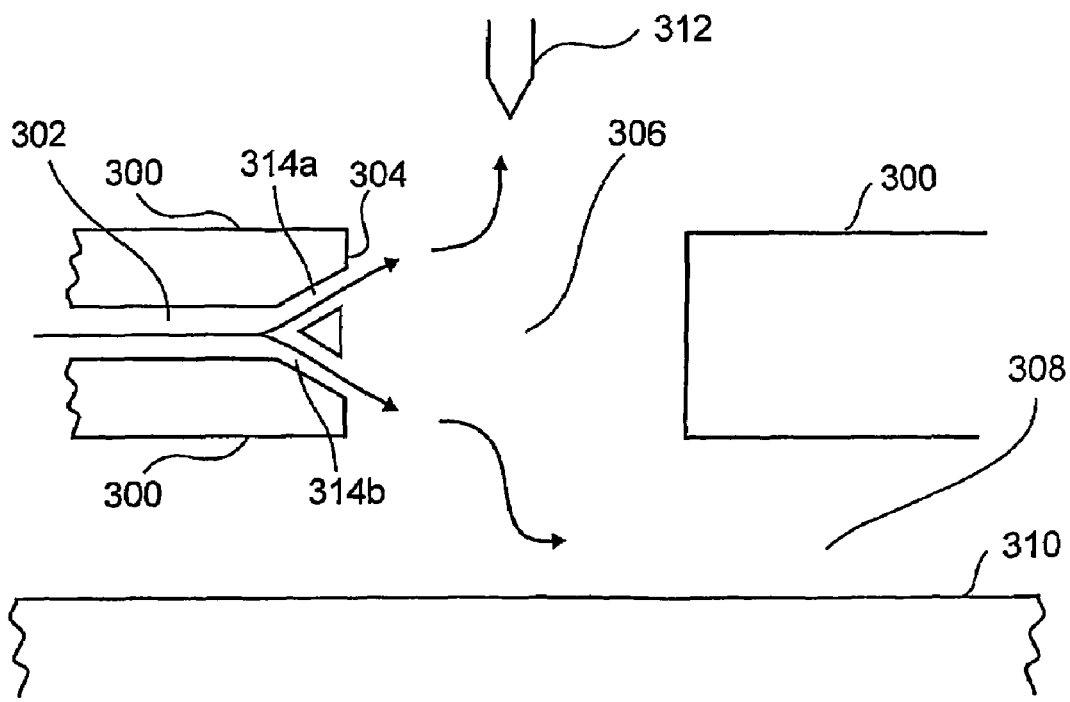
FIG. 9b is a partial cross sectional view of another domed-FAIMS apparatus including an outer electrode having a gas-directing conduit according to the instant invention.

Of course, a person of skill in the art realises that the ideas illustrated above are to be generalized to include various shapes of inner and outer electrodes, as well as various types of electrode segmentation patterns. Although the invention is described in terms of a limited number of specific embodiments in which the gas-directing conduit is provided through at least a portion of the inner electrode, it will be apparent to the person of skill in the art that some of the above-mentioned advantages are also achieved by providing a gas-directing conduit within a wall portion of an outer FAIMS electrode. For example, as shown in FIG. 9a, when the wall material of the outer electrode 300 is sufficiently thick, a channel 302 may be bored through a portion of the outer electrode 300 in a direction that is substantially perpendicular, over at least a portion of a length thereof, to a side-wall surface 304 of an ion inlet 306 into the analyzer region 308. The channel 302 is for providing a flow of a gas through the side-wall surface 304 of an ion inlet 306. A portion of the flow of a gas flows in a direction toward an ionization source 312 for desolvating ions produced at the ionization source 312, and the remaining portion of the flow of a gas flows into the analyzer region 308, between the outer electrode 300 and an inner electrode 310. Furthermore, as is shown in FIG. 9b, the opening of the channel 302 within the side-wall portion 304 of the ion inlet 306 is optionally adapted to selectively direct a portion of the flow of a gas through a first angled outlet 314a in a direction toward the ionization source 312 for desolvating ions produced thereby, whilst selectively directing the remaining portion of the flow of a gas through a second angled outlet 314b into the analyzer region 308 for transmitting the ions therethrough.

Figure 10A:
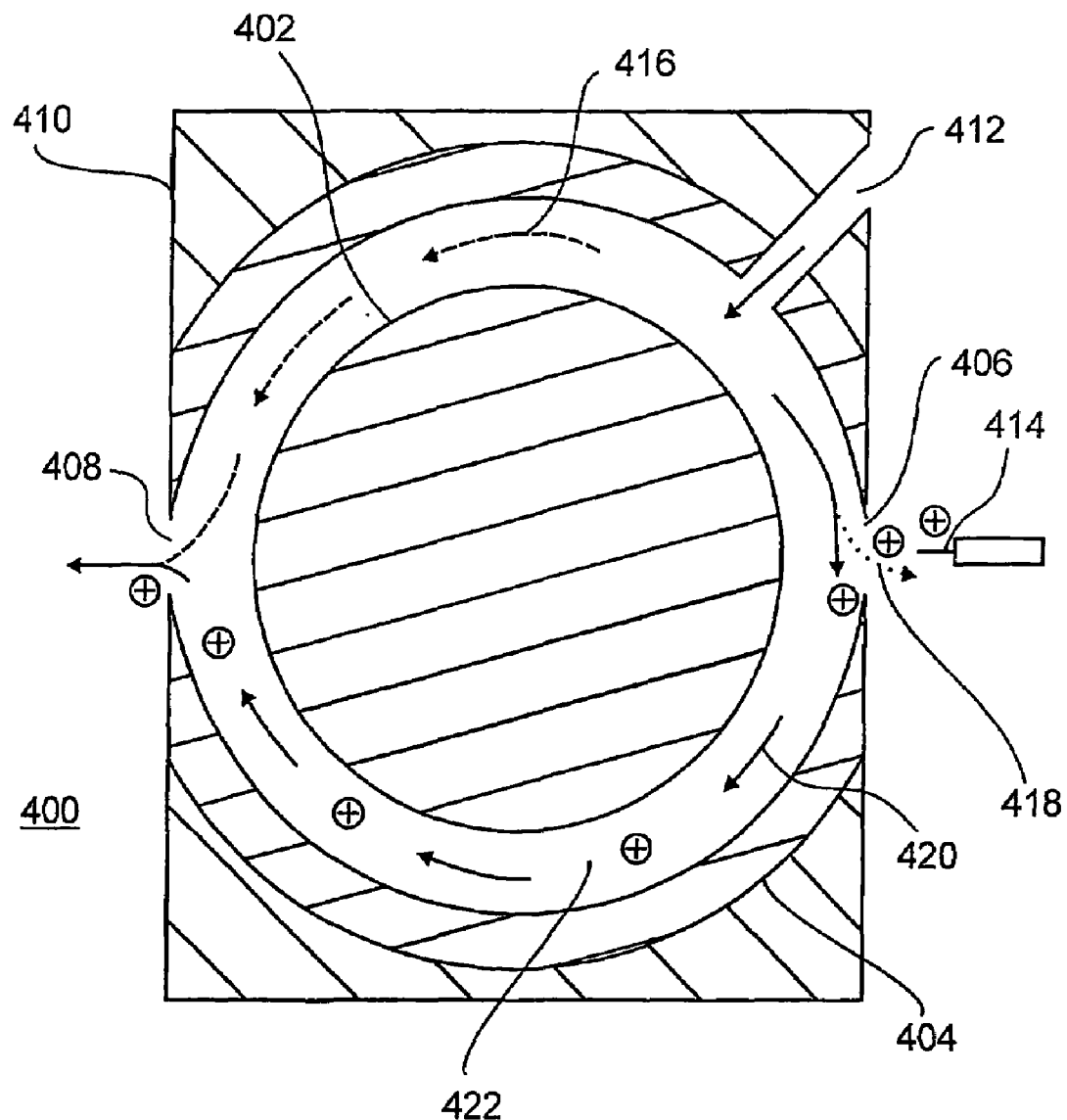
FIG. 10a is an end view of a side-to-side FAIMS including an outer electrode having a gas directing conduit according to the instant invention.

Referring now to FIG. 10a, shown is a cross sectional view of another FAIMS device according to the instant invention. The FAIMS 400 includes an inner electrode 402, an outer electrode 404, an ion inlet 406 and an ion outlet 408. In general, the inner electrode 402 has a length and an outer circumference, whereas the outer electrode 404 has a length and an inner circumference. The ion inlet 406 and ion outlet 408 are, for example, provided in the form of one of an orifice and a slit. The components of the FAIMS device are embedded in an electrically insulating material 410, such as polyetheretherketone (PEEK), which is used for maintaining the relative position of the electrodes one to the other. Typically, the FAIMS device 400 is in fluid communication with another device, for instance a not illustrated mass spectrometer detector, so that a gas flow is pulled through the FAIMS device 400 and out of the ion outlet 408.

Referring still to FIG. 10a, the FAIMS device 400 comprises a second inlet, for example a port for a gas inlet 412 through the wall of outer electrode 404 in the vicinity of the ion inlet 406. Arrows are used in the figure to illustrate the gas flows through the various portions of the FAIMS 400, with longer arrows indicating faster flow rates and shorter arrows indicating relatively slower flow rates. In particular, solid arrows designate a flow of a carrier gas, dotted arrows designate a desolvation gas flow, and dashed arrows designate "extra" gas flow. A fine-tipped electrospray needle 414 that is held at high voltage (power supply not shown) is only one component of the ionization ion source shown at FIG. 10a. Of course, any other suitable ionization ion source is used optionally in place of the electrospray ionization ion source. The gas introduced via the gas inlet 412 into the FAIMS device splits into two flows. One of the flows, the extra gas flow 416 travels around one side of the inner electrode toward the ion outlet 408. The other gas flow, comprising both the desolvation gas flow 418 and the carrier gas flow 420, travels in a direction around the other side of the inner electrode toward the ion inlet 406. In a region near the ion inlet 406, the other gas flow further splits into two flows, the desolvation gas flow 418 and the carrier gas flow 420. With sufficient volume of gas flowing outwardly from the FAIMS analyzer region 422 via the ion inlet 406, the geometry of the FAIMS device 400 shown at FIG. 10a provides a flow of gas, the desolvation gas flow 418, in a direction that is counter-current to the electrosprayed ions that are travelling toward the ion inlet 406. The desolvation gas flow 418 functions to desolvate the electrosprayed ions as they travel through the ion inlet 406 toward the analyzer region 422. This desolvation process reduces the amount of solvent and other contaminants that enter the FAIMS analyzer region, and eliminates the need of a curtain plate assembly.

As was described with reference to FIG. 2a, the high voltage that is applied to the electrospray needle 414 results in a strong electric field that directs electrosprayed ions away from the electrospray needle 414 and toward the ion inlet 406 in the outer electrode 404, through the countercurrent desolvation gas flow, and into the analyzer region 422 where the ions become entrained in the carrier gas flow stream that transports the ions through the analyzer region 422 to the ion outlet 408. The desolvation gas that flows toward the electrospray needle 414 through the ion inlet 406 aids in desolvation thereby preventing solvent and other neutrals from entering the ion inlet 406. Advantageously, the electrosprayed ions are desolvated without the need for a separate desolvation region, thereby allowing a more efficient transfer of ions into the FAIMS device 400.

Figure 10B:
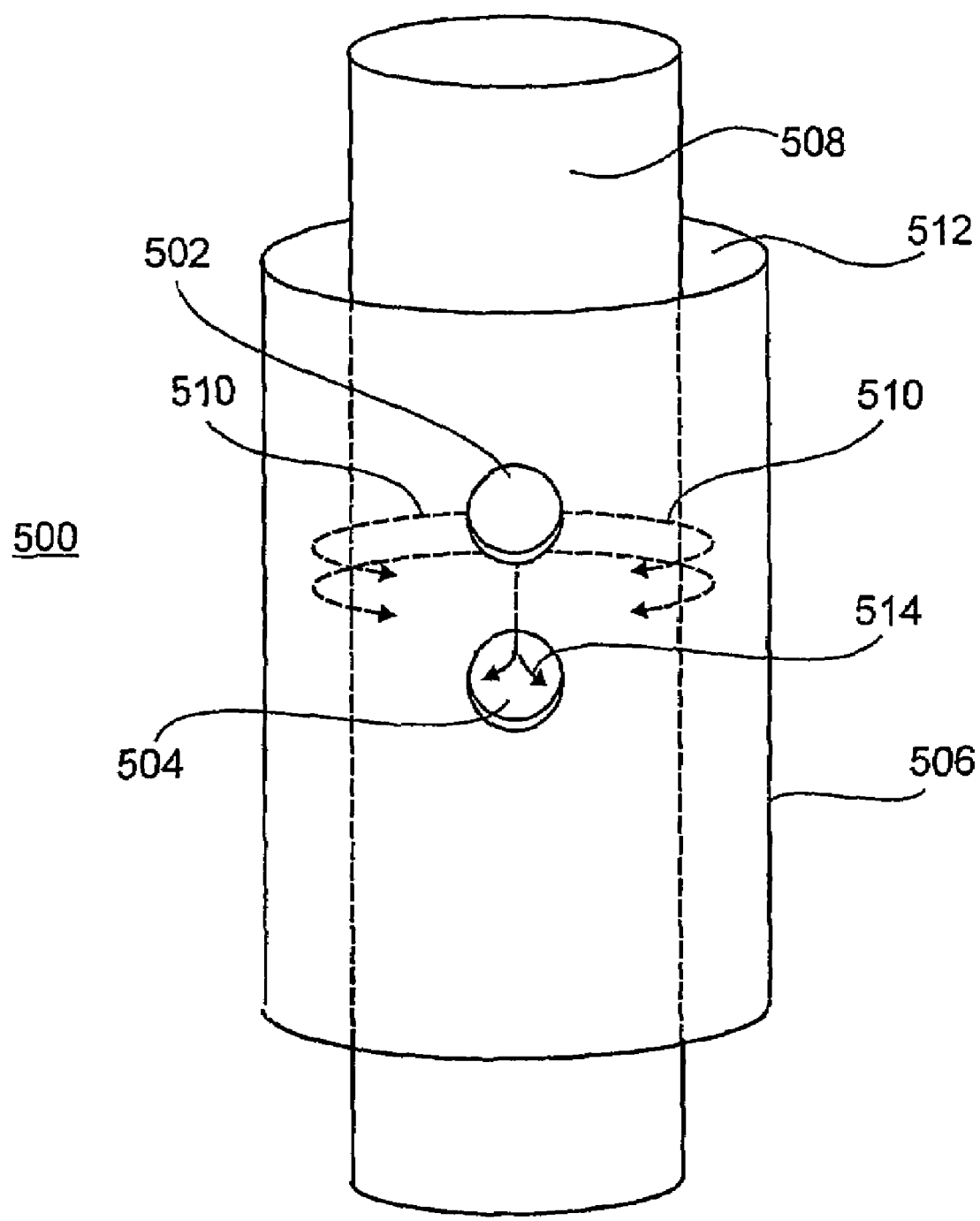
FIG. 10b is a simplified side elevational view of another side-to-side FAIMS including an outer electrode having a gas directing conduit according to the instant invention; and, FIG. 11 an end view of another side-to-side FAIMS including an outer electrode having a gas-directing conduit according to the instant invention.

Referring now to FIG. 10b, shown is a FAIMS device 500, in which a gas inlet 502 and an ion inlet 504 are positioned at 180° from an ion outlet (not shown). The ion inlet 504 and the gas inlet 502 are adjacent to each other, but rather than being adjacent along a circumference of a cylindrical outer electrode 506, the ion inlet 504 and the gas inlet 502 are adjacent to and longitudinally spaced-apart from one another along a length of the outer electrode 506. This positioning of the inlets supports a carrier gas flow 510 around both sides of an inner electrode 508, with an approximately same carrier gas flow rate in both directions around the inner electrode in a direction toward the ion outlet. With sufficient volume of gas flowing outwardly from the FAIMS analyzer region 512 via the ion inlet 504, the geometry of the FAIMS device 500 shown at FIG. 10b provides a flow of gas, the desolvation gas flow 514, in a direction that is countercurrent to the electrosprayed ions that are travelling toward the ion inlet 504. The desolvation gas flow 514 functions to desolvate the electrosprayed ions as they travel through the ion inlet 504 toward the analyzer region 512. This desolvation process reduces the amount of solvent and other contaminants that enter the FAIMS analyzer region, and eliminates the need of a curtain plate assembly. Optionally, the gas inlet 502 and the ion inlet 504 are of different size and or shape.

Figure 11:
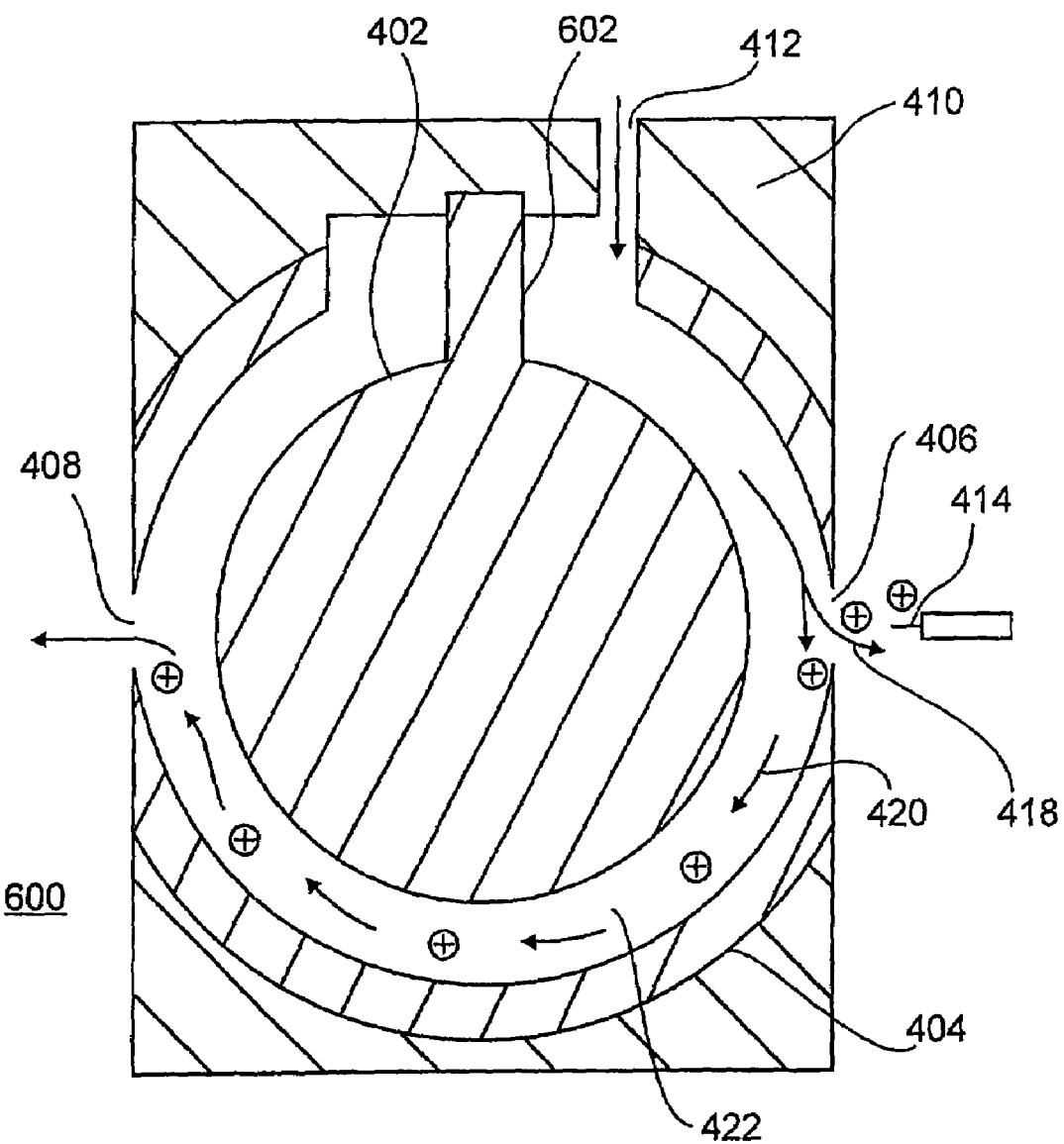

Referring now to FIG. 11, shown is another FAIMS device according to the instant invention. Elements labeled with the same numerals have the same function as those illustrated in FIG. 10a. A FAIMS device 600 includes an outer electrode 404 having a part thereof cut away to enable a protruding part 602 of the inner electrode 402 to extend into the insulating material 410. Enough of the outer electrode 404 is cut away to leave a wide enough physical space between the electrodes so as to prevent electrical discharge between the inner electrode 402 and the outer electrode 404. The shape of the protruding part 602 is optionally varied. The protruding part 602 of the inner electrode 402 forms an approximately gas tight seal with the electrically insulating material 410 to form a physical barrier which forces the gas flow, represented in the figure by a series of closed headed arrows, around one side of the inner electrode 402. Gas entering the FAIMS device 600 through the gas inlet 412 is forced to flow in a direction toward the ion inlet 406. Near the ion inlet 406, the gas flow splits with a portion of the gas travelling out toward the electrospray needle 414, forming the desolvation gas flow 418. The other portion, the carrier gas flow 420, transports ions through the FAIMS analyzer region 422, around the inner electrode 402, and to the ion outlet 408.

The blockage of flow by the modification of the inner and outer electrodes 402 and 404, respectively, results in changes in the electric fields near the modified region, causing suboptimal conditions for transmission of ions. Therefore, the blockage is advantageously located in a region away from the ion path through the FAIMS device 600 so that the changes in the electric fields caused by the protruding part 602 induce a minimal effect upon the electric fields that ions experience during their transit from the ion inlet 406 to the ion outlet 408.

The presence of the protruding part 602 results in increased carrier gas flow velocities through the analyzer region 422, with a concomitant increase of an intensity of an ion stream exiting the FAIMS device at the ion outlet 408. In particular, ion loss due to diffusion of ions into a region of the FAIMS device, which is occupied essentially with extra gas, is approximately minimized. Advantageously, FAIMS device 600, although more elaborate and intricate in its construction than the FAIMS device 400 shown at FIG. 10a, supports analysis of an ion beam having initially a low ion concentration.

Numerous other embodiments may be envisaged without departing from the spirit and scope of the invention.

What is claimed is:

1. An apparatus for separating ions, comprising:
a high field asymmetric waveform ion mobility spectrometer comprising an analyzer region defined by a space between an inner electrode and an outer electrode, the outer electrode defining an ion inlet for introducing ions into a first portion of the analyzer region and an ion outlet for extracting ions from a second portion of the analyzer region;

Characterized in that:
a gas-directing conduit is provided through at least a portion of one of the inner electrode and the outer electrode, the gas-directing conduit having an opening at a first end thereof for supporting fluid communication between the gas-directing conduit and the first portion of the analyzer region, the gas-directing conduit being adapted at a second end thereof opposite the first end for supporting fluid communication between a gas source and the gas-directing conduit.

2. An apparatus according to claim 1, wherein the gas-directing conduit comprises a channel defined within the at least a portion of the inner electrode.

3. An apparatus according to claim 2, wherein an inner surface of the channel is defined by a portion of the inner electrode.

4. An apparatus according to claim 2, wherein the channel is a bore hole through the at least a portion of the inner electrode.

5. An apparatus according to claim 1, wherein the gas-directing conduit comprises a tube supported within a volume of space defined by an inner surface of the inner electrode.

6. An apparatus according to claim 5, wherein a free length of the tube is adjustable for varying an angle of introduction of a flow of gas into the analyzer region.

7. An apparatus according to claim 1, comprising an ionization source in communication with the ion inlet.

8. An apparatus according to claim 7, wherein the ionization source is an electrospray ionization source.

9. An apparatus according to claim 7, wherein the opening at the first end of the gas-directing conduit is disposed within a portion of an outer surface of the inner electrode facing the ion inlet.

10. An apparatus according to claim 1, wherein the opening at the first end of the gas-directing conduit is disposed within a portion of an outer surface of the inner electrode facing the ion inlet.

11. An apparatus according to claim 1, wherein the opening at the first end of the gas-directing conduit is adapted to provide a flow of a gas out of the gas-directing conduit and along a predetermined direction within the analyzer region.

12. An apparatus according to claim 1 wherein, during use, at least a portion of a gas flow through the gas-directing conduit passes out of the analyzer region via the ion inlet.

13. An apparatus according to claim 1, wherein the inner electrode and the outer electrode comprise generally cylindrical coaxially aligned electrodes defining a generally annular space therebetween, the annular space forming the analyzer region.

14. An apparatus according to claim 13, wherein the analyzer region is an analyzer region of a side-to-side FAIMS apparatus.

15. An apparatus according to claim 14, comprising a barrier member disposed within a portion of the analyzer region for substantially preventing a flow of a gas through the portion of the analyzer region.

16. An apparatus according to claim 13, wherein the analyzer region is an analyzer region of a cylindrical domed-FAIMS apparatus.

17. An apparatus according to claim 1, wherein the gas-directing conduit comprises a channel defined within the at least a portion of the outer electrode.

18. An apparatus according to claim 17, wherein the analyzer region is an analyzer region of a side-to-side FAIMS apparatus.

19. An apparatus according to claim 17, wherein the outer electrode has a length and an inner surface that is curved in a direction transverse to the length, and wherein the opening at the first end of the gas-directing conduit is circumferentially spaced-apart from the ion inlet.

20. An apparatus according to claim 19, comprising a barrier member disposed within a portion of the analyzer region for substantially preventing a flow of a gas through the portion of the analyzer region.

21. An apparatus according to claim 17, wherein the outer electrode has a length and an inner surface that is curved in a direction transverse to the length, and wherein the opening at the first end of the gas-directing conduit is longitudinally spaced-apart from the ion inlet.

22. An apparatus according to claim 17, wherein the opening at the first end of the gas-directing conduit is disposed within a side-wall portion of the ion inlet within the outer electrode.

23. An apparatus according to claim 17, wherein the opening at the first end of the gas-directing conduit is adapted to direct a first portion of a flow of a gas inwardly toward the analyzer region, and to direct a second portion of the flow of a gas outwardly away from the analyzer region.

24. An apparatus according to claim 17, wherein the analyzer region is an analyzer region of a cylindrical domed-FAIMS apparatus.

25. An apparatus according to claim 22, wherein the opening at the first end of the gas-directing conduit is adapted to direct a first portion of a flow of a gas inwardly toward the analyzer region, and to direct a second portion of the flow of a gas outwardly away from the analyzer region.

26. An apparatus for separating ions, comprising:
an inner electrode having a length and an outer surface that is curved in a direction transverse to the length, the inner electrode comprising a gas outlet within the curved outer surface and at least a gas inlet, the gas outlet being in fluid communication with the at least a gas inlet via an interior portion of the inner electrode, for introducing a flow of a gas provided through the at least a gas inlet into the analyzer region;

an outer electrode having a length and a curved inner surface, the outer electrode being approximately coaxially aligned with the inner electrode, a portion of the length of the outer electrode overlapping a portion of the length of the inner electrode and forming an analyzer region therebetween, the outer electrode comprising an ion inlet within a first portion of the curved inner surface for introducing ions from an ionization source into the analyzer region and an ion outlet within a second portion of the curved inner surface for extracting ions from the analyzer region; and, an electrical controller for applying an asymmetric waveform voltage to at least one of the inner electrode and outer electrode and for applying a direct current compensation voltage to at least one of the inner electrode and outer electrode.

27. An apparatus according to claim 26, wherein the gas outlet within the curved outer surface of the inner electrode is disposed opposite the ion inlet within the first portion of the curved inner surface of the outer electrode.

28. An apparatus according to claim 26, wherein the gas outlet is in fluid communication with the at least a gas inlet via a gas-directing conduit disposed within the interior portion of the inner electrode.

29. An apparatus according to claim 28, wherein the gas-directing conduit comprises a channel defined within the interior portion of the inner electrode.

30. An apparatus according to claim 29, wherein an inner surface of the channel is defined by a portion of the inner electrode.

31. An apparatus according to claim 29, wherein the channel is a bore hole through the at least a portion of the inner electrode.

32. An apparatus according to claim 28, wherein the gas-directing conduit comprises a tube supported within the interior portion of the inner electrode.

33. An apparatus according to claim 27, comprising an ionization source in communication with the ion inlet.

34. An apparatus according to claim 33, wherein the ionization source is an electrospray ionization source.

35. An apparatus according to claim 26, wherein the analyzer region is an analyzer region of a side-to-side FAIMS apparatus.

36. An apparatus according to claim 35, comprising a barrier member disposed within a portion of the analyzer region for substantially preventing a flow of a gas through the portion of the analyzer region.

37. An apparatus according to claim 26, wherein the analyzer region is an analyzer region of a cylindrical domed-FAIMS apparatus.

38. A method for separating ions, comprising the steps of:
providing a FAIMS analyzer region defined by a space between inner and outer spaced apart electrodes;
producing ions at an ionization source that is in fluid communication with the analyzer region via an ion inlet within the outer electrode;
introducing the ions produced at an ionization source into the FAIMS analyzer region via the ion inlet within the outer electrode;

providing a flow of a gas into the analyzer region through at least a first portion of the inner electrode such that a first portion of the flow of a gas flows out of the analyzer region through the ion inlet.

39. A method according to claim 38, wherein the first portion of the flow of a gas flows counter-current to a direction that ions are traveling in the vicinity of the ion inlet.

40. A method according to any one of claims 38, comprising a step of adjusting a rate of the flow of a gas, such that the first portion of the flow of a gas substantially desolvates the ions introduced into the FAIMS analyzer region via the ion inlet within the outer electrode.

41. A method according to claim 39, wherein a second portion of the flow of a gas flows through the FAIMS analyzer region toward the ion outlet in the outer electrode.

42. A method according to claim 38, wherein the step of providing a flow of a gas includes a step of directing the flow of a gas in a direction that is approximately toward the ion inlet within the outer electrode.

43. A method according to claim 38, comprising a step of varying an orientation of the at least a first portion of the inner electrode relative to the ion inlet within the outer electrode.

44. A method according to claim 41, comprising a step of entraining the desolvated ions within the second portion of the flow of a gas.

45. A method according to claim 38, comprising a step of applying an asymmetric waveform voltage to at least one of the inner electrode and the outer electrode and applying a direct current compensation voltage to at least one of the inner electrode and the outer electrode.

46. A method according to claim 38, wherein the FAIMS analyzer region is an analyzer region of a side-to-side FAIMS.

* * * * *